(12) United States Patent
Salagnad et al.

(10) Patent No.: US 7,803,950 B2
(45) Date of Patent: Sep. 28, 2010

(54) METHOD FOR THE PRODUCTION OF DIARYLCYCLOALKYL DERIVATIVES

(75) Inventors: Christophe Salagnad, Les Angles (FR); Frank Zocher, Alsbach-Hahnlein (DE); Andreas Burgard, Frankfurt (DE); Bernd Junker, Bad Soden (DE); Rolf Hoerlein, Frankfurt (DE); Thomas Stuedemann, Kelkheim (DE); Claus-Jügen Maier, Weinheim (DE); Jochen Hachtel, Frankfurt (DE); Wolfgang Holla, Kelkheim (DE); Christoph Tappertzhofen, Frankfurt (DE); Berndt Kulitzscher, Esselbach (DE); Stephane Mutti, Le Perreux sur Marne (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 684 days.

(21) Appl. No.: 11/676,721

(22) Filed: Feb. 20, 2007

(65) Prior Publication Data

US 2007/0197614 A1    Aug. 23, 2007

Related U.S. Application Data

(63) Continuation of application No. PCT/EP2005/009095, filed on Aug. 23, 2005.

(30) Foreign Application Priority Data

Aug. 23, 2004  (DE) ................. 10 2004 040 736

(51) Int. Cl.
*C07D 263/32* (2006.01)
*C12P 7/62* (2006.01)
(52) U.S. Cl. .................... 548/236; 548/228
(58) Field of Classification Search .............. None
See application file for complete search history.

(56) References Cited

U.S. PATENT DOCUMENTS

| | | | | |
|---|---|---|---|---|
| 5,728,899 A | * | 3/1998 | Curran et al. | 568/838 |
| 7,094,795 B2 | * | 8/2006 | Holla et al. | 514/374 |
| 7,153,878 B2 | * | 12/2006 | Conner et al. | 514/365 |
| 2007/0197788 A1 | * | 8/2007 | Holla et al. | 546/14 |

FOREIGN PATENT DOCUMENTS

| WO | WO 03/020269 | 3/2003 |
|---|---|---|
| WO | WO 2004/075815 | 9/2004 |
| WO | WO 2004/076390 | 9/2004 |
| WO | WO 2005/040394 | 5/2005 |

OTHER PUBLICATIONS

Bannard, R. A. B., et. al., Utility of the Dehalogenation-Deetherification Sequence for the Proof of Structure of Methoxyhalocyclohexanols and Methoxyhalocyclopentanols. Synthesis of the Cis- and Trans-2 and 3-Methoxycyclohexanols and -cyclopentanols, Canadian Journal of Chemistry, vol. 45, No. 21, pp. 2605-2611 (1967).

Bernasconi, C., et. al., Stereoselective Photolysis of 2-(.alpha.-tetrahydropyranyloxy)-3-tetrahydropyrones, Journal of Heterocyclic Chemistry, vol. 17, No. 1, pp. 44-48 (1980).

Curran, T.T., et. al., The Preparation of Optically Active 2-Cyclopenten-1,4-Diol Derivatives from Furfuryl Alcohol, Tetrahedron, Elsevier Science Publishers, vol. 53, No. 6 pp. 1983-2004.

Davies, W., et. al., The Chlorination and Bromination of the Toluic Acides and the Preparation od the Phthalaldehydic Acids, J. Chem. Soc. vol. 121, pp. 2202-2215 (1922).

Dimroth, K., et. al., Uber Tetrahydro-resorcin (3-Oxy-Cyclohexanon)., Ber. (1942) vol. 75, pp. 322-326.

Gatti, R. G. P., et. al., Palladium-Catalysed Enantiodivergent synthesis of cis- and trans-4-aminocyclohex-2-enols, J. Chem. Soc. Perkins Trans. 1: Organic and Bio-Organic Chemistry vol. 4, pp. 577-584, (1997).

Goto, Y., et. al., Studies on Azole Compounds. III. Reactions of Oxazole N-Oxides with Phosphoryl Chloride and Acetic Anhydride, Chem. Pharm. Bull. vol. 19, No. 10, pp. 2050-2057 (1971).

Harada, T., et. al., Enantiodifferentiating Functionalization of Cis-Cycloalkane-1,2-diols and cis-endo-5-Norbornen-2,3-ylenebis(Methanol) via Chiral Spiroacetals Derived from 1-Menthone, Journal of Organic Chemistry American Chemical Society vol. 54, No. 11 (1989) pp. 2599-2605.

(Continued)

*Primary Examiner*—Fiona T Powers
(74) *Attorney, Agent, or Firm*—Jiang Lin

(57) ABSTRACT

The invention relates generally to a process for preparing diarylcycloalkyl derivatives of the formula (I).

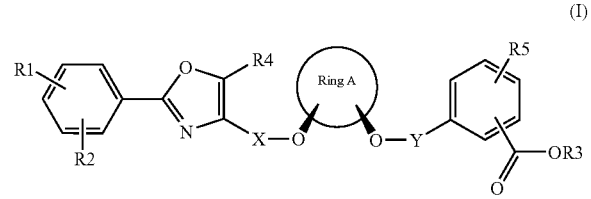

wherein the respective R-group substituents are defined herein. These compounds of formula (I) are activators for peroxisome proliferator-activated receptors (PPAR activators) which are useful in the therapeutic treatment of a number of diseases and disorders of the central nervous system such as multiple sclerosis, Parkinson's Disease, psychiatric disorders and the like. The present invention is a novel process for preparing PPAR activators of the formula (I) which do not have the disadvantages of the processes known in the prior art. In particular, a process is provided with which the PPAR activators of formula (I) can be prepared in a suitable enantiomeric excess, i.e. high enantioselectivity, without the need for subsequent chiral chromatography.

7 Claims, No Drawings

Hirata, T., et. al., Asymmetric Hydrolyses of 1,2- and 1,3-Diacetoxycyclohexanes with the Cultured Suspension Cells of Marchantia Polymorpha, Chirality, vol. 9, pp. 250-253 (1997).

Johnson, C.R., et. al., Enzymatic Asymmetrization of Meso-2-Cycloalken-1,4-diols and Their Diacetates in Organic and Aqueous Media, Tetrahedron Letters vol. 33, No. 48, (1992) pp. 7287-7290.

Larock, R. C., et. al., Halogenation of Alcohols, Comprehensive Organic Transformations VCH Publishers, (1989) pp. 353-363.

Larock, R.C., et. al., Halogenation of Hydrocarbons, Comprehensive Organic Transformations VCH Publishers, Inc., (1989) pp. 311-313.

Laumen, K., et. al., A Facile Chemoenzymatice Route to Optically Pure Building Blocks for Cyclopentanoid Natural Products, Journal Chemical Society, Chem. Commun. (1986) pp. 1298-1299.

Lehtonen, A. et. al., The Separation of Cis- and Trans-1,3-Cyclohexanediol Isomers by Copper Complexation. Crystal Structures of Cis-1,3-Cyclohexanediol and Coppper (II) Chloride cis-1,3-Cyclohexanediol Complex, Polyhedron, vol. 21, (2002) pp. 1133-1138.

Mattson, A., et. al., Kinetic Resolution of Chiral Auxiliaries with C2-Symmetry by Lipase-Catalyz Alcoholysis and Aminoylsis, Acta Chemica Scandinavica, (1996) pp. 918-921 vol. 50, No. 10.

Nara, M., et. al., Stereochemical Studies—LVII. Synthesis of Optically Active Compounds by the Novel use of Meso-Compounds 1. Efficient Synthesis of two Structural Types of Optically Pure Prostaglandin Intermediates, Tetrahedron vol. 36 No. 22, pp. 3161-3170 (1980).

Nicolosi, G., et. al., Desymmetrization of cis-1,2-Dihydroxycycloalkanes by Stereoselective Lipase Mediated Esterification, Tetrahedron Asymmetry, vol. 6, No. 2, (1995) pp. 519-524.

Patti, A., et. al., Enantioselective Synthesis of (-)- and (+)—Conduritol F via Enzymatic Asymmetrization of cis-Cyclohexa-3,5-diene-1,2-diol, J. Org. Chem. (1996) vol. 61, pp. 6458-6461.

Perkins, W. H., et. al., An Investigation of the Action of Halogens on 2:4-Dimethylbenzoyl Chloride, J. Chem. Soc. vol. 127, pp. 2275-2297 (1925).

Rigby, W., et. al., The Resorcitols., J. Chem. Soc.. pp. 1586-1588 Part. III, (1949).

Simiti, I., et. al., Die Delepine-Reaktion bei 2-Aryl-4-Chlormethyl-Oxazolen , Arch. Pharmaz. vol. 304, (1971) pp. 425-429.

Theil, F., et. al., Investigation of the Pancreatin-Catalyzed Acylation of cis-Cyclopent-2-ene-1,4-diol with Various Trichloroethyl and Vinyl Alkanoates, Liebigs Ann. Chem. (1991) pp. 195-200, vol. 3.

* cited by examiner

METHOD FOR THE PRODUCTION OF DIARYLCYCLOALKYL DERIVATIVES

CROSS-REFERENCE TO RELATED APPLICATIONS

This application is a continuation of International Patent Application No. PCT/EP2005/009095 filed on Aug. 23, 2005 which is incorporated herein by reference in its entirety which also claims the benefit of priority of German Patent Application No. 10/2004 040736.3 filed on Aug. 23, 2004.

FIELD OF THE INVENTION

The invention relates generally to a process for preparing diarylcycloalkyl derivatives of the formula (I). which are useful in the therapeutic treatment of a number of diseases and disorders of the central nervous system such as multiple sclerosis, Parkinson's Disease, psychiatric disorders and the like. More specifically, the present invention further relates to novel intermediates which are formed in the process according to the invention, to processes for preparing intermediates of compounds of the formula (I) and to a process for separating cis/trans-isomer mixtures of starting materials which are used in the preparation of compounds of formula (I)

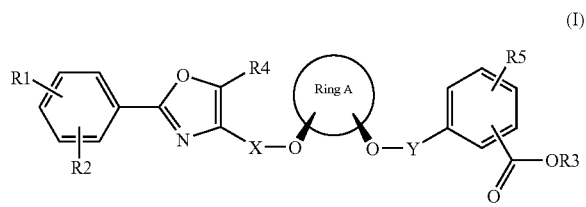

wherein the R-group substituents are defined herein.

BACKGROUND OF THE INVENTION

The compounds of formula (I) are activators for peroxisome proliferator-activated receptors (PPAR activators) and are already known from WO 03/020269. Of the PPAR activators described in WO 03/020269, effective PPAR activators have been found to be those which have a cis substitution of the X- and Y-containing substituent on the central ring A. This applies in particular to compounds in which the ring A=cyclohexyl, preferably cis-1,3-cyclohexyl.

In the synthesis and isolation of the desired target molecules of formula (I), principally two factors present difficulties. One is the cis/trans isomerism of the substituents of ring A. Since, in the case of the compounds of the formula (I), the cis-isomers are more effective PPAR activators than the corresponding trans-isomers, it is advisable to remove the particular trans-isomers of the ring A in the corresponding intermediates actually at the start of the synthesis in order to avoid unnecessary yield losses. Secondly, considering only the cis-isomer of the ring A, it also must to be taken into account that two chiral carbon atoms are present in most intermediates and in the target molecule of the of the formula (I), it must also be recognized that ring A is substituted by two different radicals (X, Y). Consequently, in the connection of ring A with, for example, the X-containing substituent, a racemic mixture is formed in an equimolar reaction because this substituent can in principle be connected to both functional groups of ring A. If no allowance is made for this, the compounds of the formula (I) are also present as a racemic mixture.

Although it is possible using the preparation process described in WO 03/020269 for PPAR activators to prepare the compounds of the formula (I) in enantiomerically pure form in principle, the process described therein has some significant disadvantages. Poisonous tin compounds, cesium fluoride and iodide-containing compounds are used in the reaction and disposal of these is also necessary. The process involves a racemic synthesis, i.e., after removal of the enantiomer (which is not required by chiral chromatography), at least half of the expensive starting materials are lost as waste. Moreover, the chiral chromatography additionally has to be linked to achiral chromatography; half of the product or the valuable starting materials used therefore are lost in a racemate separation into two enantiomers. The "wrong" enantiomer cannot be recycled and has to be disposed of as waste. Finally, the process requires the use of sodium hydride as a base and N,N-dimethylformamide as a solvent both of which may result in potentially exothermic decomposition.

In order to be able to prepare an enantiomeric excess or an enantiomerically pure compound of formula (I), chiral chromatography is absolutely necessary in the process described in WO 03/020269. Especially on the industrial scale, the high costs associated with chiral chromatography are found to be the main disadvantage of this process.

An alternative process for preparing the PPAR activators as disclosed in WO 03/020269 is described in the international application WO10/308350.2. In this process, which is restricted to the preparation of cis-1,3-disubstituted cyclohexane derivatives, cis-1,3-cyclohexanediol is initially alkylated either with a protecting group (benzyl or silyl) or one of the two substituents of the target molecule, in which case the racemic mixture of the corresponding monoalkylated cis compound is formed. This intermediate is in turn reacted with an acyl donor, and this monoalkylated and monoacylated intermediate which is also present as a racemate is separated via an enzymatic ester cleavage and subsequent chromatography into two fractions from which the two enantiomers of the target molecule can each be synthesized separately. Alternatively, the racemic monoalkylated intermediate can be separated by enzymatic ester formation and subsequent chromatography into two fractions from which the two enantiomeric forms of the target molecule can in turn be synthesized in two separate batches. A disadvantage in this process is that in spite of the avoidance of chiral chromatography, a racemic intermediate is initially formed, from which the two enantiomeric forms of the target molecule inevitably are produced. When the synthesis variant is utilized by means of the protecting group introduced first, the benzyl-containing protecting groups have to be removed by hydrogenation. In this hydrogenation, the first substituent of the target molecule which has already been bonded to the corresponding intermediate may be removed again to a certain degree, which leads to a yield loss. Silyl-containing protecting groups are removed with fluoride, but this too leads to further side reactions in the remaining substituents of the corresponding intermediates and should consequently be avoided.

The use of enzymes to separate racemic mixtures of various compounds (starting materials or intermediates) is well known in the art. However, the discovery of suitable enzymes for the enantioselective separation of the racemic mixture to be separated in each case presents particular difficulties.

For instance, T. Hirata et al., Chirality 9: 250-253 (1997) describes the hydrolysis of cis- and trans-1,3-diacetoxycyclohexane to acyloxycyclohexanols in the presence of cultivated plant cells from common liverwort (*Marchantia polymorpha*). However, to achieve this, the cultivation of the plant cells is necessary; the accompanying enzymes are not known.

The enantiomeric excess in the hydrolysis of meso-cis-1,3-diacetoxycyclohexane here is only 15% for (1R,3S)-1-acetoxycyclohexan-3-ol. trans-1,3-Diacetoxycyclohexane is converted to (1R,3R)-3-acetoxycyclohexan-1-ol (60% yield) with 27% enantiomeric excess and cyclohexane-1,3-diol (70% yield). This method is therefore not suitable for preparing an acceptable enantiomeric excess or enantiomerically pure cis-1S-acyloxycyclohexan-3R-ol.

K. Laumen et al., J. Chem. Soc., Chem. Commun., (1986) 1298-1299 describe the enzymatic hydrolysis of cis-1,4-diacetoxycyclopent-2-ene in the presence of lipases such as *Pseudomonas* species or *Mucor miehei*. At a conversion of approx. 50%, a monoacylated enantiomer with an enantiomeric purity of from 95 to 97% is formed. The enantiomeric purity can be increased to above 99% by recrystallization.

SUMMARY OF THE INVENTION

The invention relates generally to a process for preparing diarylcycloalkyl derivatives of the formula (I).

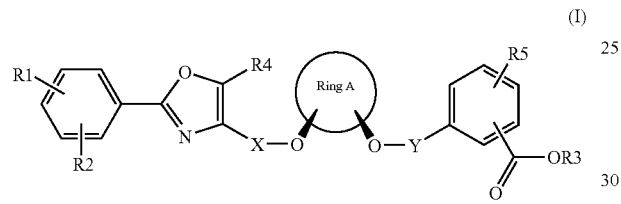

(I)

wherein the respective R-group substituents are defined below. These compounds of formula (I) are activators for peroxisome proliferator-activated receptors (PPAR activators) which are useful in the therapeutic treatment of a number of diseases and disorders of the central nervous system such as multiple sclerosis, Parkinson's Disease, psychiatric disorders and the like. The present invention is a novel process for preparing PPAR activators of the formula (I) which do not have the disadvantages of the processes known in the prior art. In particular, a process is provided with which the PPAR activators of formula (I) can be prepared in a suitable enantiomeric excess, i.e. high enantioselectivity, without the need for subsequent chiral chromatography.

DETAILED DESCRIPTION OF THE INVENTION

The invention relates generally to a process for preparing diarylcycloalkyl derivatives of the formula (I) by an enzymatically-driven process which does not have the disadvantages of the processes known in the prior art. i.e., a process is which the compounds of formula (I) can be prepared in a suitable enantiomeric excess, i.e. high enantiomeric-selectivity, without the need for subsequent chiral chromatography.

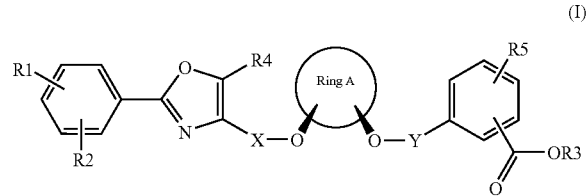

(I)

The inventive process of the present invention also does not require the use of poisonous and toxic reaction components which are dangerous to use, dispose of and consequently, environmentally hazardous.

This is achieved by a process for preparing a compound of formula (I), comprising the following steps, in which:
a1) a compound of the formula (IX) is reacted with water to give a compound of the formula (V) in the presence of an enzyme which affords a suitable enantiomeric excess of compound (V), or
a2) a compound of the formula (X) is reacted with at least one acyl donor to give compound (V) in the presence of an enzyme which affords a suitable enantiomeric excess of compound (V),
b) compound (V) is reacted in the presence of an acidic catalyst with a compound which can form the base-stable and acid-labile protecting group Z3 to yield the compound of formula (VIII) and,
c) compound (VIII) is converted in the presence of a nucleophile to a compound of formula (II),
d) compound (II) is reacted in the presence of a base B1 with a compound of the formula (VI) to give a compound of the formula (IIIa) or with a compound of the formula (VII) to give a compound of the formula (IIIb),

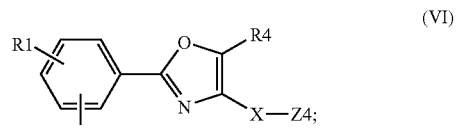

(VI)

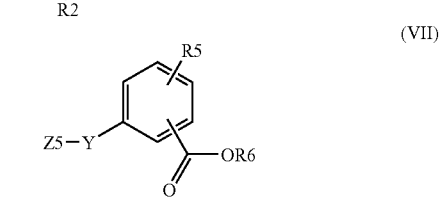

(VII)

e) compound (IIIa) is converted to a compound of formula (IVa) or compound (IIIb) to a compound of formula (IVb), the particular reaction carried out with an alcohol in the presence of an acidic catalyst,
f) compound (IVa) is reacted with compound (VII) or compound (IVb) with compound (VI) to give a compound of the formula (Ia) in the presence of the base B1 and
g) if appropriate, the compound (Ia) is hydrolyzed or hydrogenated to compound (I) when R3 is H, resulting in:

compounds (IX) and (X) each being present as the pure cis isomer or as cis/trans mixtures, The variables and substituents are each defined as follows:
Ring A is $C_3$-$C_8$-cycloalkyl or $C_3$-$C_8$-cycloalkenyl, in which one or more carbon atoms in the cycloalkyl or cycloalkenyl rings may be optionally replaced by oxygen atoms,
R1, R2, R4 and R5 are each independently selected from the group consisting of H, F, Cl, Br, OH, $NO_2$, $CF_3$, $OCF_3$, $C_1$-$C_6$-alkyl and —O—($C_1$-$C_6$-alkyl),
R3 is independently selected from the group consisting of H, $C_1$-$C_6$-alkyl or benzyl, which may optionally be substituted by F, Cl, Br, OH, $NO_2$, $CF_3$, $OCF_3$, $C_1$-$C_6$-alkyl or —O—($C_1$-$C_6$-alkyl),
R6 is $C_1$-$C_6$-alkyl or benzyl, which may optionally be substituted by F, Cl, Br, OH, $NO_2$, $CF_3$, $OCF_3$, $C_1$-$C_6$-alkyl or —O—($C_1$-$C_6$-alkyl), X is $C_1$-$C_6$-alkyl, in which one or more carbon atoms in the alkyl group may be replaced by oxygen atoms, Y is $C_1$-$C_6$-alkyl, in which one or more carbon atoms in the alkyl group may be replaced by oxygen atoms, Z1 and Z2 are each independently an acid-stable protecting group, Z3 is a base-stable and acid-labile protecting group, Z4 and Z5 are independently each a leaving group, B1 is a tertiary alkaline earth metal alkoxide, tertiary alkali metal alkoxide, alkaline earth metal amide, alkali metal amide, alkaline earth metal silazide, alkali metal silazide or alkali metal hydride.

The compounds mentioned in the above process steps arise from the following scheme I which serves to illustrate the process according to the invention.

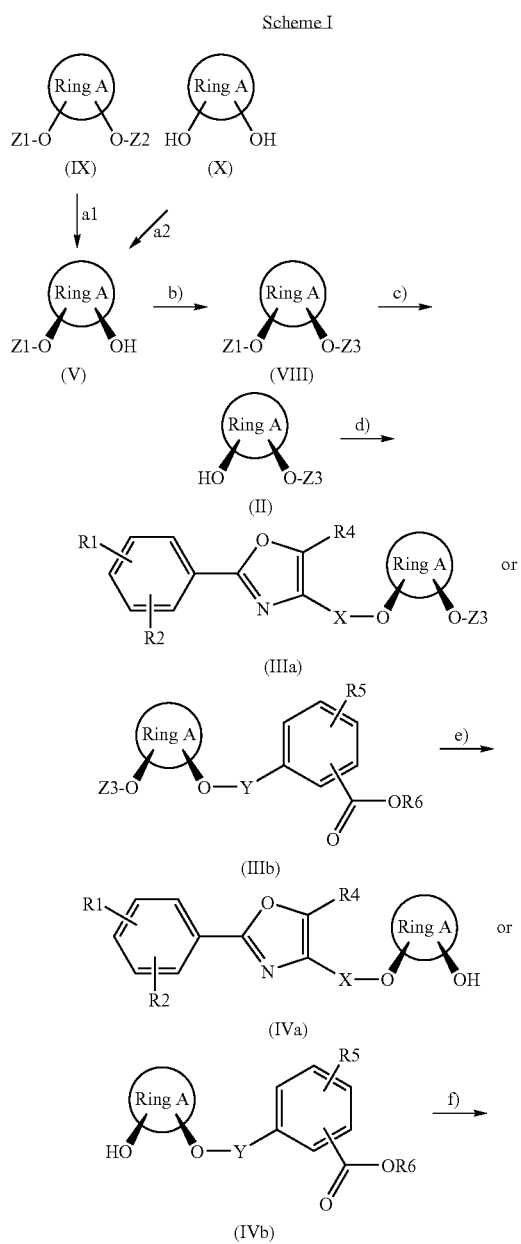

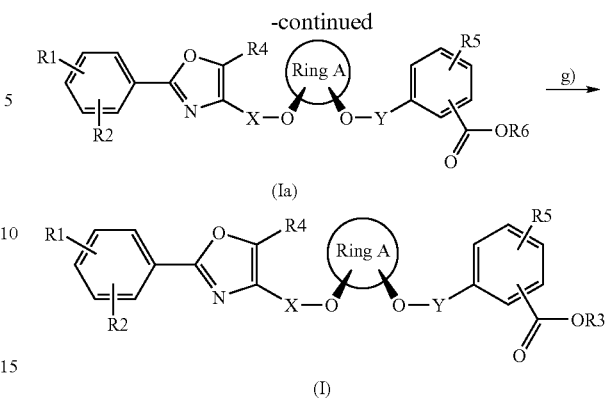

The process steps shown in scheme I are described in detail below.

With respect to compounds (I to VIII) shown in scheme I, a cis substitution of these substituents in relation to ring A is present with regard to the two substituents bonded to the ring A (in the particular compounds). For example, it may be a cis-1,2-, cis-1,3- or cis-1,4-substitution. Preference is given in this context to cis-1,2- and cis-1,3-substitution, and greater preference to cis-1,3-substitution. Particular preference is given to cis-1,3-substitution on the cyclohexyl ring A. For the sake of simplicity, the ring A or else the substituents X and Y are referred to below as simple radicals (alkyls or alkenyls) even when, depending on the manner of viewing, it is conceivable in the case of ring A to name it as an alkane or alkene (ring A as the basic fragment of the formula (I)) or as an alkylene or alkenylene.

Suitable enantiomeric excess (high enantioselectivity) shall refer to an enantiomeric purity (ee) of greater than 50% ee, preferably greater than 90% ee, more preferably greater than 95% ee, even more preferably greater than 98% ee, much more preferably greater than 99% ee and particularly preferably greater than 99.5% ee.

Preferably, steps a1) and/or a2) are carried out in the presence of lipase B from *Candida antarctica*.

The process of the invention has advantages over those of the prior art that, by virtue of the use of the preferred enzymes, the chiral information is introduced into the particular precursors at the start of the process, a result of which is that these precursors are already present enantioselectively in a suitable, in some cases even in extremely high, enantiomeric excess (enantiomeric purity>99% ee). Consequently, the desired enantiomers of the compounds (I) may also be prepared enantio-selectively in a suitable, in some cases even in extremely high, enantiomeric excess (enantiomeric purity>99% ee). Accordingly, compared to the processes known in the prior art, no yield loss of up to 50% is observed and also no separation of the racemic mixtures of the cis-enantiomers of the corresponding intermediates is required in order to prepare a desired enantiomer of the compounds (I) in a suitable enantiomeric excess.

Surprisingly, the chiral configurations of the molecules formed as early as the start of the synthesis (in some cases >99% enantiomeric purity of the precursors), owing to the protecting group Z3 which is stable under basic conditions, is preserved in spite of two alkylation steps from which the chiral PPAR activator of the formula (I) is prepared, whose enantiomeric purity is thus likewise >99% ee. In addition, the enzymes used in the process according to the invention enable the starting materials used to be not only in the form of the particular pure cis isomer, but also as cis/trans mixtures, without the enantiomeric purity of the intermediates or of the target molecule being impaired. When cis/trans mixtures of the starting materials are used in the process according to the invention, the corresponding trans starting compounds, owing to the protecting group technique used in the purification of the intermediates, for example by extraction, can be removed without any problem. Additional purification steps, for example with chromatography, are not required in addition for this purpose.

Compared to the synthesis route disclosed in WO 03/020269, the following advantages of the present invention may be emphasized. When a suitable lipase is selected, it is possible, by enzymatic desymmetrization, to form virtually pure enantiomer (>99% ee) of compound (V) which, as a chiral starting material, is an important building block for the stereoselective synthesis of the PPAR activators of formula (I) with optical purities of >99% ee; the stereochemical molecular configurations are surprisingly preserved with the aid of a suitable protecting group technique up to the chiral PPAR activator to be prepared, so that not more than half of the valuable starting materials has to be disposed of as waste. Moreover, a complicated racemate separation using chiral chromatography is no longer required and the use and disposal of poisonous tin compounds, iodide-containing compounds and cesium fluoride are also no longer necessary. Finally the use of sodium hydride as a base and N,N-dimethylformamide as a solvent are also no longer necessary and chromatography separations are if at all, only required in a small degree.

It is also important to note that by using lipase B from *Candida antarctica* in step a1) of the process of the present invention, it is possible to realize a conversion of >90% to achieve enantiomeric purities of >99% ee in solution, without a recrystallization being required for this purpose.

It is possible by the process according to the invention to prepare compounds of formula (I)

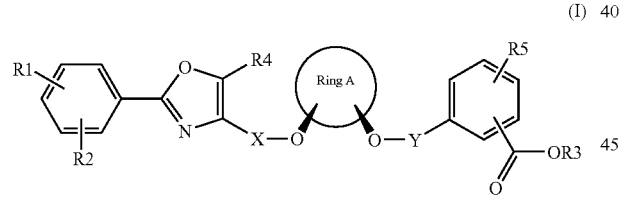

(I)

in which:
Ring A is $C_3$-$C_8$-cycloalkyl or $C_3$-$C_8$-cycloalkenyl, in which one or more carbon atoms in the cycloalkyl or cycloalkenyl rings may optionally be replaced by oxygen atoms,
R1, R2, R4 and R5 are each independently selected from the group consisting of H, F, Cl, Br, OH, $NO_2$, $CF_3$, $OCF_3$, $C_1$-$C_6$-alkyl and —O—($C_1$-$C_6$-alkyl),
R3 is H, $C_1$-$C_6$-alkyl or benzyl, which may optionally be substituted by F, Cl, Br, OH, $NO_2$, $CF_3$, $OCF_3$, $C_1$-$C_6$-alkyl or —O—($C_1$-$C_6$-alkyl),
X is $C_1$-$C_6$-alkyl, in which one or more carbon atoms in the alkyl group may be replaced by oxygen atoms,
Y is $C_1$-$C_6$-alkyl, in which one or more carbon atoms in the alkyl group may be replaced by oxygen atoms.

Preferably, it is possible by the process according to the invention to prepare compounds of the formula (I) in which:
Ring A is cyclopentyl, cyclohexyl or cycloheptyl,
R1, R2, R4 and R5 are each independently selected from the group consisting of H, F, Cl, Br, OH, $NO_2$, $CF_3$, —$OCF_3$, $C_1$-$C_6$-alkyl and O—$C_1$-$C_6$-alkyl,
R3 is H or $C_1$-$C_6$-alkyl or benzyl
X and Y are each independently $C_1$-$C_6$-alkyl.

More preferably, it is possible by the process according to the invention to prepare compounds of the formula (I) in which:
Ring A is cyclohexyl in which the X-containing and the Y-containing substituents of formula (I) are in the cis-1, 3-arrangement relative to the cyclohexyl fragment,
X and Y are each methyl.

Even more preferably, it is possible by the process according to the invention to prepare compounds of the formula (I) in which:
Ring A is cyclohexyl in which the X-containing and the Y-containing substituents of formula (I) are in the cis-1, 3-arrangement relative to the cyclohexyl fragment, and the carbon atom of ring A which is substituted by the Y-containing substituent has an R configuration,
X and Y are each methyl.

Most preferably, it is possible by the process of the present invention to prepare compounds of formula (I), in which:
Ring A is cyclohexyl in which the X-containing and the Y-containing substituents of formula (I) are in the cis-1, 3-arrangement relative to the cyclohexyl fragment, and the carbon atom of the ring A which is substituted by the Y-containing substituent has R configuration,
X and Y are each methyl,
R1, R2 and R4 are each independently selected from the group consisting of H, F, Cl, $C_1$-$C_3$-alkyl and —O—($C_1$-$C_3$-alkyl),
R5 is H or $C_1$-$C_3$-alkyl.

The compound (IX) shown in scheme I, which can be used as a starting material in the process according to the invention, may in turn be prepared by:
i) reacting compound (X) with at least one acyl donor in the presence of an enzyme which affords mainly the cis isomer of compound (IX), and the trans isomers of the compounds of the formula (V) which may be formed as by-products which are subsequently removed, or
ii) reacting the compound (X) with at least one acyl donor.

Preferably, step i) is carried out in the presence of a lipase from the *porcine pancreas*, a lipase from a *Burkholderia* species, a lipase from *Pseudomonas cepacia* or a lipase from *Pseudomonas* species.

With reference to scheme I, the process according to the invention is illustrated by way of example below in the context of a reaction sequence to be made in a typical manner, including the precursors.

Step a)
In the inventive process, compounds (V) are prepared by step a), for which purpose several routes are available. The compounds (V) are well known in the literature. See for example, K. Dimroth et al., Ber. (1942), 75B, 322-6 wherein the monoacetate of acyloxycyclohexanols is disclosed. In the publication of T. Hirata et al. cited at the outset, it is additionally stated how various cis-1S-acyloxycyclohexan-3R-ols can be isolated by chiral chromatography. The main problem in this context can be seen in the separation of the compounds (V) into the individual enantiomers, which presents very great difficulties in practice, since principally chiral chromatography has to be used for this purpose.

a) Enzymatic Acylation
As an alternative to chiral chromatography, the individual enantiomers of the compounds (V) may be prepared by enzymatic acylation from compounds (X). The compounds (X) may be used either as cis/trans isomer mixtures or as pure cis isomers and are commercially obtainable in these forms from various suppliers (for example from Merck, Fluka or Aldrich). When the compounds (X) are used in the form of the pure cis isomer, this has the disadvantage that they first have to be isolated from the corresponding cis/trans mixtures and that the pure cis isomers are more expensive. To separate cis/trans mixtures of compounds (X), it is possible, for example in the case of 1,3-cyclohexanediol, to utilize a crystallization as the cis-1,3-cyclohexanediol-copper complex (W. Rigby, J. Chem. Soc. (1949), 1586: R. Sillanpää et al., Polyhedron 21 (2002), 1133-1138).

Starting from compounds (X), the enzymatic acylation in the process according to the invention may be carried out in the presence of various enzymes (for example lipases) with an acyl donor. It is possible in this context to use a single acyl donor or a mixture of a plurality of acyl donors. The reaction may be effected either without additional organic solvent (example 1) or with an additional organic solvent (example 2). Useful organic solvents for this purpose are in principle all common organic solvents, such as toluene, chlorinated hydrocarbons or ethers, preferably methyl tert-butyl ether. However, the reaction cannot be carried out in water. Suitable acyl donors are all chemical compounds which can form an acid-stable protecting group Z1 or Z2. Listed by way of example for this purpose are carboxylic esters. Preferably suitable therefor are vinyl esters such as vinyl acetate, isopropenyl acetate, vinyl laurate or vinyl butyrate, more preferably vinyl acetate or isopropenyl acetate.

For the enzymatic acylation, the enzyme used may not be any desired enzyme. Instead, an enzyme has to be used with which the desired target molecule can be prepared either directly or indirectly in a suitable enantiomeric excess. In addition, it depends upon the enzyme used whether the compounds (V) are formed directly from the compounds (X) or whether (indirectly) first the compound (IX) is formed and in turn subsequently has to be converted to compound (V). When a lipase is used which stems from fraction B of the organism *Candida antarctica* (referred to below as lipase B from *Candida antarctica*, separation of the fractions according to EP-A 287 634), preference is given to starting from a cis/trans isomer mixture of the compound (X) and forming the cis monoacyl compound (V), while the diacyl compound (IX) is obtained only as a by-product. In contrast, when lipase B from *Candida antarctica* is used, no trans monoacyl compound (V) is obtained, because the corresponding trans starting compound (X) is either not converted or is converted to the corresponding diacyl compound (IX).

The direct conversion (enzymatic acylation) of a compound of the formula (X) to a compound of the formula (V) is preferably carried out in the presence of lipase B from *Candida antarctica*. Particular preference is given to carrying out this conversion in the presence of a lipase selected from Chirazyme L2 lyo., Chirazyme L2 c.f. C2 or Chirazyme L2 c.f. C3. The assignment of the aforementioned enzymes (in the form of their trade name) to the accompanying accession number of the GenBank of the National Center for Biotechnology Information (NCBI) can be taken from the table 1 shown in example 1.

The reaction mixture of compounds of the formulae (IX) and (V) obtained in this reaction may, if appropriate, be separated by extraction, distillation or chromatography. In order to achieve an enantiomeric excess, the separation is, however, not necessarily required at this point, because the compound (IX) formed as a by-product cannot be provided with a protecting group Z3 in the step b) which follows.

Accordingly, the by-product (IX) is double-deprotected in step c) of the process according to the invention and, if appropriate, removed by extraction in the workup of the compound (II). A similar view can be taken for the unconverted reactant (X) which can be removed by extraction, distillation or chromatography actually in this process step, or in the workup of the compounds (II) or (IX).

Instead of lipase B from *Candida antarctica*, it is also possible in the enzymatic acylation to use a lipase from the *porcine pancreas*, a lipase from *Burkholderia cepacia*, a lipase from *Burkholderia* species, a lipase from *Pseudomonas cepacia* or a lipase from *Pseudomonas* species. When these lipases are used, both compounds (IX) and (V) are formed from the reactant (X). However, the monoacyl compounds (V) are not present in the desired trans form, while the compounds (IX) which are likewise formed are surprisingly present predominantly as cis diacyl. These cis diacyl compounds (IX) may, as explained below, be converted by enzymatic desymmetrization (enzymatic hydrolysis) to the desired cis enantiomers of the compound (V).

The conversion of a compound (X) by enzymatic acylation to a compound (IX) which is present mainly as a cis isomer is preferably carried out in the presence of a lipase selected from a lipase from the *porcine pancreas*, a lipase from *Burkholderia cepacia*, a lipase from *Burkholderia* species, a lipase from *Pseudomonas cepacia* or a lipase from *Pseudomonas* species. More preferably, the lipase is selected from a lipase from the *porcine pancreas*, a lipase from *Burkholderia cepacia*, a lipase from *Burkholderia* species or *Pseudomonas cepacia*. Much more preferably, the lipase is selected from Chirazyme L1 lyo. Chirazyme L1 c.f., Chirazyme L7 lyo or Lipase PS. Particularly preferably, the lipase is selected from Chirazyme L1 lyo., Chirazyme L1 c.f. or Chirazyme L7 lyo. The assignment of the aforementioned enzyme trade names to their NCBI accession number can be taken from table 1.

In order to achieve an enantiomeric excess, it is, however, necessary that the trans compound (V) formed as an undesired by-product in this synthetic route is removed from the compound (IX) by extraction, distillation or, if appropriate, chromatography when the reactant (X) is used as a cis/trans mixture. However, this workup step can be dispensed with when the compound (X) is used as the pure cis isomer. Preference is given to carrying out any removal of the by-product (V) by extraction. Since the subsequent enzymatic desymmetrization of the compound (IX) is carried out with a different enzyme and in aqueous phase, the enzyme used in the enzymatic acylation should be removed beforehand, for example by filtration. The enzyme is preferably removed before the removal of the monoacyl compound (V-trans).

Chemical Acylation/Enzymatic Desymmetrization

A further possible starting point for the preparation of the compounds (V) are the compounds (IX) which are likewise commercially available in the form of cis/trans isomer mixtures or as the pure cis isomer from various suppliers (for example Merck, Fluka or Aldrich). cis/trans isomer mixtures can be separated, for example in the case of cis-1,3-diacetoxycyclohexane, can be separated by distillation as a result of the boiling point of the two isomers which differs by 1° C. However, owing to the often low boiling point differences, this process is complicated and expensive. As mentioned above, the compounds (IX) may be obtained from the compounds (X) by enzymatic acylation. Alternatively, the compounds (X) may also be reacted directly with the above acyl donors (in the absence of enzymes) to give the compounds (IX). This reaction has already been known for some time and is referred to as chemical acylation which does not, however, proceed stereoselectively (examples 3 and 4). The chemical acylation may, for example, be carried out with acetic anhydride/4-dimethylaminopyridine (4-DMAP), triethylamine (TEA) in dichloromethane. The chemical acylation may be carried out either with a single acyl donor or an acyl donor mixture; preference is given to using a single acyl donor, so that the substituents Z1 and Z2 in the compound (IX) have the same definition.

The compounds (IX) may be reacted with water to give the compound (V) in the presence of an enzyme which affords a suitable enantiomeric excess of the compound (V). The enzyme used is preferably lipase B from *Candida antarctica*. Particular preference is given to carrying out this reaction in the presence of a lipase selected from Chirazyme L2 lyo., Chirazyme L2 c.f. C2 or Chirazyme L2 c.f. C3. This reaction has to be carried out in aqueous solution; the exclusive use of organic solvents is not suitable here. Surprisingly, the trans diacyl compound (IX) is not converted by lipase B from *Candida antarctica*.

Consequently, it is possible by these two methods (enzymatic acylation and chemical desymmetrization) and the likewise possible combination of these two methods (enzymatic acylation with subsequent enzymatic desymmetrization) to use a cis/trans isomer mixture of the compounds (X) for the preparation of an enantiomeric excess or of an enantiomerically pure cis monoacyl compound (V). This process is less expensive than the use of the pure cis isomer (X). The preparation of enantiomerically pure compounds (V) is thus further provided by the present invention. Enantiomerically pure compounds shall refer in the context of the present invention to compounds which have a purity of >98% (ee>98%), preferably >99% (ee>99%), more preferably >99.5% (ee>99.5%).

The great advantage in the use of lipase B from *Candida antarctica* can be seen in that, irrespective of whether a single acyl donor or a mixture of acyl donors is used, the compound (V) is always formed in enantiomerically pure form. In the compounds (IX), (V) and (XIII), the protecting groups Z1 and Z2 are each independently an acid-stable protecting group. The protecting groups Z1 and Z2 preferably have the same definition. Z1 and Z2 are preferably —C(O)—R, R is optionally substituted alkyl or aryl, for example $C_1$-$C_6$-alkyl or phenyl. Z1 and Z2 are more preferably each independently —C(O)—($C_1$-$C_3$-alkyl), particularly preferably —C(O)—$CH_3$. The lipase B from *Candida antarctica* may be used either in its non-immobilized form (Chirazym L2) or in its immobilized forms (c.f., c.f.C2, c.f.C3, manufacturer: Roche Diagnostics).

The lipase B from *Candida antarctica* is also obtainable from other manufacturers, for example Novozymes (Novozym 435 as an immobilized substance). Alternatively, it is also possible to use dissolved lipase B from *Candida antarctica*, for example Novozym CALB L or Novozym 525 F after immobilization of the enzyme.

The above-described separation processes of cis/trans mixtures of the compounds (X) or (IX), and the preparation process of an enantiomeric excess of a cis compound (V) or of an enantiomerically pure cis compound (V) find use in accordance with the invention in particular by converting the enantiomeric excess of a cis compound (V) or an enantiomerically pure cis compound (V) by a suitable protecting group technique and further alkylation steps to the desired target molecules (I) (in enantiomeric excess or enantiomerically pure), for which neither chiral nor achiral chromatography is necessary.

All attempts to achieve a selective O-alkylation of the enantiomerically pure compound (V) have to date failed, since an inter- and intramolecular migration of the acyl group was to be observed under the unavoidable basic alkylation conditions (acyl=e.g. acetyl, benzoyl). An attempt is therefore being made to use a base-stable protecting group technique, for example tetrahydropyranyl, methoxyisopropyl as the protecting group, so that the chiral information which has been generated in compound (V) by the enzymatic desymmetrization is preserved in spite of the basic acylation conditions. A controlled alkylation sequence and protecting group strategy allows, as a further part of the subject matter of the present invention, the preparation of the desired stereoisomeric PPAR activator, surprisingly without loss of the chiral information.

Step b)

The compound (V) is reacted in the presence of an acidic catalyst with a compound which can form a base-stable and acid-labile protecting group Z3 to give the compound of the formula (VIII). The acidic catalysts used may, for example, be inorganic acids, toluenesulfonic acid, pyridinium para-toluenesulfonate or acidic ion exchangers such as Amberlyst H15. Preference is given to using pyridinium para-toluenesulfonate for this purpose. The protecting group Z3 present in the compound (VIII) is a base-stable and acid-labile protecting group. It is preferably an acetal or ketal protecting group. Z3 is more preferably tetrahydropyranyl or methoxyisopropyl, particularly preferably tetrahydropyranyl. A suitable compound which can form the base-stable and acid-labile protecting group Z3 is preferably 3,4-dihydro-2H-pyran. One equivalent of the compound (V) is reacted with from 1 to 10 equivalents of the compound which forms the base-stable and acid-labile protecting group Z3, preferably with from 1.1 to 1.4 equivalents. The acidic catalyst is used generally at from 0.01 to 1 equivalent, preferably at from 0.05 to 0.1 equivalent. The reaction temperature is usually from 20 to 80° C., preferably from 50 to 60° C. Like all other steps of this process, step b) is usually carried out at standard pressure. Suitable solvents for step b) are organic solvents, for example chlorinated hydrocarbons, carboxylic esters such as ethyl acetate, carboxamides such as N-methylpyrrolidone, ether compounds such as diethyl ether or methyl tert-butyl ether, aromatic hydrocarbons such as chlorobenzene or toluene. Alternatively, 3,4-dihydro-2H-pyran itself may also be used as the solvent. A preferred solvent is toluene. In contrast, water or alcohols are not possible solvents, since they react, for example, with 3,4-dihydro-2H-pyran to give the corresponding acetals. The compound (VIII) formed in this step can be distilled for purification, but it can be used without further purification in the next process step.

Step c)

The compound (VIII) is converted in the presence of a nucleophile to the compound (II). For this reaction, referred to as deacylation, the nucleophile used may, for example, be an alkali metal or alkaline earth metal alkoxide, preferably sodium methoxide. For one equivalent of the compound (VIII), from 0.1 to 10 equivalents of nucleophile are used; preference is given to catalytic amounts of from 0.1 to 0.3 equivalent. The reaction temperature is usually from 10 to 80° C., preferably from 15 to 25° C. This deacylation step may be performed in all organic solvents which do not react with the nucleophile (sodium methoxide), for example aromatic hydrocarbons, alcohols, chlorinated hydrocarbons. Preference is given to toluene as the solvent, since it is possible in the preceding process step too to extract with toluene, so that no solvent change is needed in the deacylation, and it is likewise possible to carry out the alkylation in the subsequent step d) with toluene. The compound (II) may be distilled for purification, which is, though, not absolutely necessary.

Step d)

The compound (II) is reacted in the presence of a base B1 with a compound of the formula (VI) to give a compound of the formula (IIIa) or with a compound of the formula (VII) to give a compound of the formula (IIIb). Suitable bases B1 are tertiary alkaline earth metal alkoxides, tertiary alkali metal alkoxides, alkaline earth metal amides, alkali metal amides, alkaline earth metal silazides, alkali metal silazides or alkali metal hydrides. In contrast, primary or secondary alkoxides are not suitable. Preferred bases B1 are potassium tert-butoxide (KOtBu), tertiary isopentoxide, lithium diisopropylamide or potassium bis(trimethylsilyl)amide. Particular preference is given to potassium tert-butoxide or potassium bis(trimethylsilyl)amide. Suitable solvents are organic aprotic solvents, for example ether compounds (diethyl ether, methyl tert-butyl ether), carboxamides (N-methylpyrrolidone), aromatic hydrocarbons (chlorobenzene or toluene); preference is given to toluene. The reaction is carried out normally at from 20 to 80° C., preferably at from 50 to 60° C. In this reaction, normally 1 equivalent of the compound (II) is reacted with from 1 to 3 equivalents of alkylating agent (compounds (VI) or (VII)), preferably from 1.1 to 1.3 equivalents of alkylating agent. The base B1 is used at from 1 to 3 equivalents, preferably from 1.5 to 2 equivalents.

The alkylating reagents of the formulae (VI) or (VII) are commercially available or may be prepared by a literature method. Z4 and Z5 are each independently a leaving group. It is possible in this context to use all common leaving groups; preference is given to chlorine or bromine. Preparation processes for compounds of the formula (VI) can be found, for example, in WO 03/020269 or in the international application with the application number 10308350.2, or in The Chemistry of Heterocyclic Compounds (Ed.: A. Weissberger, E. C. Taylor): Oxazoles (Ed:. I. J. Turchi), b). Methoden der Organischen Chemie [Methods of Organic Chemistry], Houben-Weyl, 4th edition, Hetarene III, subvolume 1; c) I. Simit, E. Chindris, Arch. Pharm. 1971, 303, 425; d). Y. Goto, M. Yamazaki, M. Hamana, Chem. Pharm. Bull. 1971, 19 (10), 2050-2057. The compounds of the formula (VII) are likewise described in the two aforementioned applications, and also in WO 00/64888 (isobutyl esters) and WO 00/64876 (methyl esters). In addition, these compounds may be prepared by free-radical side-chain halogenation (see literature overview: R. C. Larock, Comprehensive Organic Transformations, p. 313, 1989 VCH Publishers, Inc.) or from the alcohols or derivatives preparable therefrom (see literature overview: R. C. Larock, Comprehensive Organic Transformations, p. 353-363, 1989 VCH Publishers, Inc.). Also known (see J. Chem. Soc. 1925, 127, 2275-2297; J. Chem. Soc. 1922, 121, 2202-2215) is the preparation of various 2-bromomethylbenzoyl bromides by free-radical bromination, which can then converted by further reaction with alcohols to the bromomethylbenzoic esters belonging to the group of the alkylating reagents of the formula III.

The decision as to whether alkylation is effected in step d) with the compound (VI) or the compound (VII) depends upon the enantiomer desired as the target molecule (1). Preference is given to reacting the compounds (II) with the compound of the formula (VI), especially when the ring A is cis-1,3-cyclohexyl.

Step e)

The compound (IIIa) is converted to the compound (IVa) or the compound (IIIb) is converted to the compound (IVb), the particular reaction being effected with an alcohol in the presence of an acidic catalyst. Suitable acidic catalysts are the same compounds which have already been listed in step b), and the acidic catalysts can be selected independently in step b) and e). Suitable alcohols are preferably primary alcohols, in particular methanol. This step is carried out at a temperature of from 20 to 80° C., preferably from 45 to 55° C. Suitable solvents are the organic aprotic solvents already listed under step d), preferably toluene. The solvent in step d) and e) can be selected independently. One equivalent of the compounds (III) is reacted with from 0.01 to 10 equivalents of acid, preferably 0.05 equivalent of, for example, hydrochloric acid. The alcohols used are used at from 1 to 3 equivalents. The compound (IV) formed in this step may be distilled for purification. When this compound is crystalline, preference is given to purification by crystallization; purification by means of chromatography is less preferred, since excessively high use of solvent is needed for this purpose.

Step f)

In step f), the compound (IVa) is reacted with the compound (VII) or the compound (IVb) is reacted with the compound (VI) to give the compound (Ia) in the presence of the base B1. The base B1 is selected independently of step d), but preference is given to using the same base as in step d). In principle, the same solvents as in step d) may also be used, the solvent selection likewise being independent of step d). In addition to toluene, the solvent selected in this second alkylation step may preferably also be chlorobenzene, preference being given here to chlorobenzene owing to a greater conversion compared to toluene. The ratios of starting compounds, alkylating agents and base B1 used correspond to those of step d). The reaction is carried out usually at from −30 to +20° C., preferably at from −5 to +5° C.

Step g)

This step is required only when the R3 radical in the target molecule of the formula (I) is hydrogen, i.e., the desired PPAR activator should be present in the form of the free acid. Otherwise, the compound (Ia) obtained in step f) corresponds to the compound (I). However, when this is not the case, the compound (Ia) is converted to the compound (I) by hydrolysis or hydrogenolysis. The hydrolysis may be carried out by common processes, either under basic conditions (R6 is preferably n-alkyl) or under acidic conditions (R6 is preferably tert-butyl). When R6 is a benzyl radical, the compound (I) is preferably obtained by a hydrogenolysis with methods known to those skilled in the art. In the case of the basic hydrolysis, metal hydroxides, for example alkali metal or alkaline earth metal hydroxides, are used in a ratio of from 1 to 10 equivalents to the compounds to be hydrolyzed. Suitable solvents are water, alcohols or further organic solvents, for example ether compounds (diethyl ether, methyl tert-butyl ether), carboxamides (N-methylpyrrolidone) or aromatic hydrocarbons. Preference is given to using tert-butanol. The reaction temperature is from 20 to 100° C., preferably from 65 to 75° C. Subsequently, acidification of the carboxyl function, for example with organic or inorganic acids, preferably with hydrochloric acid, releases the desired chiral PPAR activator of the formula (I) in an enantiomeric purity of >99% ee. If appropriate, a recrystallization with organic solvents, for example aromatic solvents, preferably toluene, ether acetate or n-butyl acetate, or if appropriate with carboxylic esters, alkyl ethers or alkyl alcohols, may also be carried out. This recrystallization may likewise be carried out after step e).

When steps b) to g) are all carried out in the same solvent, preference is given to using toluene for this purpose.

In a preferred embodiment, the process according to the invention comprises the following steps:
 a) a compound of the formula (IX) is reacted in the presence of lipase B from *Candida antarctica* with water to give a compound of the formula (V),
 b) the compound (V) is reacted in the presence of an acidic catalyst with a compound which can form the base-stable and acid-labile protecting group Z3 to give the compound of the formula (VIII) and
 c) the compound (VIII) is converted in the presence of a nucleophile to a compound of the formula (II),
 d) a compound (II) is reacted in the presence of a base B1 with a compound of the formula (VI) to give a compound of the formula (IIIa),
 e) the compound (IIIa) is converted to a compound of the formula (IVa), the reaction being effected with an alcohol in the presence of an acidic catalyst,
 f) the compound (IVa) is reacted with the compound (VII) to give a compound of the formula (Ia) in the presence of the base B1 and
 g) if appropriate, the compound (Ia) is hydrolyzed or hydrogenolyzed to the compound (I) when R3 is H.

This preferred embodiment of the process according to the invention is suitable in particular for the preparation of compounds of the formula (I) in which the ring A is cyclohexyl in which the X-containing and the Y-containing substituents of formula (I) are in the cis-1,3-arrangement relative to the cyclohexyl fragment, and the carbon atom of the ring A which is substituted by the Y-containing substituent has R configuration.

Alternatively, in this preferred embodiment, the compound (V) may be prepared by enzymatic acylation with a suitable lipase from compound (X) as described above, but preference is given to the compound (IX) as the starting point. Compound (IX) in turn can be prepared by enzymatic acylation with a suitable lipase from compound (X) or preferably via chemical acylation from compound (X).

A typical reaction sequence to be set up, including the preceding stages, is illustrated below by way of example for these preferred embodiments. It is possible by this reaction sequence in particular to prepare compounds of the formula (I) in which the ring A is cyclohexyl, the two X- and Y-containing substituents are arranged in the cis-1,3-arrangement relative to the ring A and the carbon atom of the ring A which is substituted by the Y-containing substituents has R configuration. The process conditions described in the particular synthetic stages, for example for the acids, bases or solvent used, also apply to the remaining compounds of the formula (I) in which the ring A is not restricted to cis-1,3-cyclohexane derivatives.

In addition, the scheme (II) which follows illustrates this typical reaction sequence for the preparation of this selection of PPAR activators. The starting materials are either isomerically pure cis-1,3-cyclohexanediol (X-i-cis) (from Clariant) or a cis/trans isomer mixture (X-i) (from Acros), cis-1,3-Cyclohexanediol can, if appropriate, be obtained by means known to those skilled in the art from a cis/trans-cyclohexanediol isomer mixture, for example by chromatography. 1,3-Cyclohexanediol can be converted either by an enzymatic acylation directly to cis-1S-acyloxycyclohexan-3R-ol (V-i) or by chemical acylation via 1,3-diacyloxycyclohexane (IX-i) as an intermediate. Both in the chemical and in the enzymatic acylation, preference is given to converting only one of the above-described acyl donors, so that the acid-stable protecting groups Z1 and Z2 in formula (IX-i) have the same definitions. 1,3-Diacyloxycyclohexane is also commercially available as the cis isomer (IX-i-cis) or as a cis/trans mixture (from Clariant), cis-1,3-Diacyloxycyclohexane or the cis/trans mixture (IX-i) is converted by an enzymatic desymmetrization (enzymatic hydrolysis) as described above to the virtually enantiomerically pure cis-1S-acyloxycyclohexan-3R-ol (>99% ee) (V-i), cis-1S-Acyloxycyclohexan-3R-ol is then acetalized, for example, with 3,4-dihydro-2H-pyran or methoxypropene in the presence of acidic catalysts, for example inorganic acids, toluenesulfonic acid, pyridinium para-toluenesulfonate or acidic ion exchangers to give cis-1S-acyloxy-3R—O-tetrahydropyranylcyclohexane (VIII-i where Z3=tetrahydropyranyl). After deacylation with nucleophiles, for example organic amines or inorganic alkali metal, alkaline earth metal hydroxides or alkoxides to give cis-O-tetrahydropyranylcyclohexan-3S-ol (II-i), the alkylation with an oxazole halide (VI-i where Z4=halide) then takes place in the presence of one of the above-described inorganic or organic bases to give cis-1S—O-oxalyl-3R—O-tetrahydropyranylcyclohexane (IIIa-i). It is pointed out here that the two variables X and Y are shown for reasons of clarity as a methyl fragment in the following scheme in the formulae (IIIa-i; IVa-i, VI-i, VII-i, Ia-i and I-i). However, this is not a restriction, since this reaction sequence can also be performed with all other definitions of the variables X and Y. cis-1S—O-Oxalyl-3R—O-tetrahydropyranyl-cyclohexane (IIIa-i) is then converted using primary alcohols, for example methanol, ethanol, in the presence of acidic catalysts, for example inorganic acids, toluenesulfonic acid, pyridinium para-toluenesulfonate, Amberlyst-H15 to cis-3S-oxazylcyclohexan-1R-ol (IVa-i) which is alkylated, for example, with alkyl bromobenzoates (VII-i where Z4=Br) under basic conditions (compound of the formula (Ia-i) and finally hydrolyzed to give the compound of the formula (I-i) when R3=H. If R3=R6=$C_1$-$C_6$-alkyl or benzyl in the desired target molecule, the hydrolysis step need no longer be carried out because the compound (Ia-i) corresponds in this case to the compound (I-i). The hydrolysis may be carried out under acidic conditions or under basic conditions. The basic hydrolysis is suitable preferably for R6=n-alkyl, in which case hydrolysis is effected with metal hydroxides, for example alkali metal or alkaline earth metal hydroxides, in suitable solvents, for example water, alcohols, organic solvents, to give the desired stereoisomers of the PPAR activators, and the carboxylic acid group is released by acidification. When R6=tert-butyl, the hydrolysis is preferably carried out under acidic conditions. Alternatively, the compound (I-i) can also be prepared by hydrogenolysis of the compound (1a-i). This is a possibility in particular when R6=benzyl and the corresponding compound (I-i) where R3=H is desired.

Scheme II:
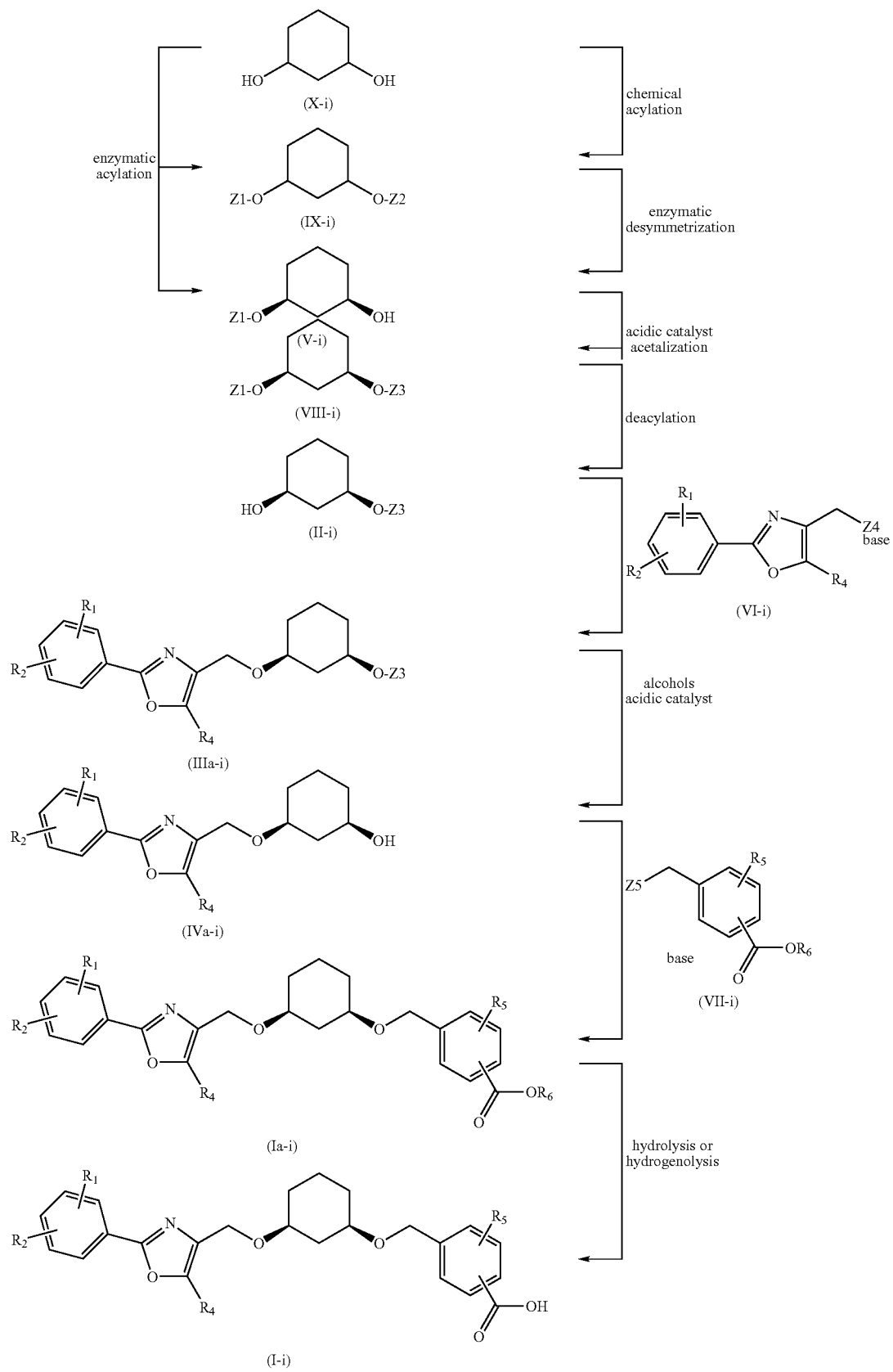

As is apparent from the remarks regarding step a) of the process according to the invention, the provision of a process for preparing a compound of the formula (V) forms a further part of the subject matter of the present invention

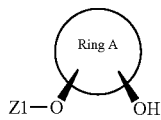

(V)

in which a1) a compound of the formula (IX) is reacted in the presence of lipase B from *Candida antarctica* with water to give a compound of the formula (V),

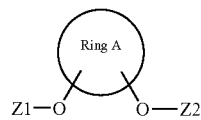

(IX)

a2) a compound of the formula (X) is reacted in the presence of lipase B from *Candida antarctica* with at least one acyl donor to give the compound (V),

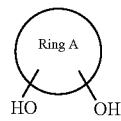

(X)

and the compounds (IX) and (X) are each present as the pure cis isomer or as a cis/trans mixture, if appropriate, the trans isomer of the compound (IX) is removed after step a1) or the trans isomer of compound (X) is removed after step a2), and in which the variables and substituents are each defined as follows:

Ring A is $C_3$-$C_8$-cycloalkyl or $C_3$-$C_8$-cycloalkenyl, in which one or more carbon atoms in the cycloalkyl or cycloalkenyl rings may be replaced by oxygen atoms, Z1 and Z2 are each independently an acid-stable protecting group.

Preferably, in the compounds (V), the ring A is cis-1,3-cyclohexyl, where the carbon atom of the ring A which has the OH substituent has R configuration, and Z1 and Z2 are each —C(O)—($C_1$-$C_3$-alkyl).

The present invention further relates, with reference to the remarks on step a), thus also to a process for separating a cis/trans mixture of a compound of the formula (X), wherein

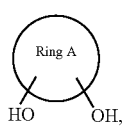

(X)

-continued

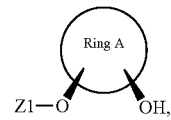

(V)

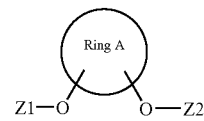

(IX)

i) the compound (X) is reacted with at least one acyl donor to give a compound of the formula (IX) and the compound (IX) is reacted with water to give a compound of the formula (V) in the presence of an enzyme which affords a suitable enantiomeric excess of the compound (V), and the compound (V) formed is subsequently separated by chromatography, extraction or distillation from the unconverted trans isomer of the compound (IX) and any other by-products formed, or ii) the compound (X) is reacted with at least one acyl donor to give a compound (V) in the presence of an enzyme which affords a suitable enantiomeric excess of the compound (V), and the compound (V) formed is subsequently separated by chromatography, extraction or distillation from the unconverted trans isomer of the compound (X) and any other by-products formed, or iii) the compound (X) is reacted with at least one acyl donor to give a compound (IX) in the presence of an enzyme which affords mainly the cis isomer of the compound (IX), and the cis isomer of the compound (IX) is subsequently separated by chromatography, extraction or distillation from the trans isomer of the compound (V) which is likewise formed and any other by-products formed, in which the isolated fractions of the compounds (IX) and (V) are if appropriate converted in the presence of a nucleophile by detachment of the protecting group Z1 and/or Z2 to the corresponding compound (X), and in which the variables and substituents are each defined as follows:

Ring A is $C_3$-$C_8$-cycloalkyl or $C_3$-$C_8$-cycloalkenyl, in which one or more carbon atoms in the cycloalkyl or cycloalkenyl rings may be replaced by oxygen atoms, Z1 and Z2 are each independently an acid-stable protecting group.

For the other by-products which are mentioned in the process options i) to iii) and may be formed, depending on the selected process option, for example, the trans isomer of the compound (IX), the trans isomer of the compound (V) or the cis isomer of the compound (IX) are possible. These other by-products which, depending on the reaction, are only formed in some cases, and also any reactant still present, may be removed from the main fractions which occur in each case by methods known to those skilled in the art, possibly in the form of additional chromatography, extraction or distillation steps.

In this separation process, preference is given to carrying out the particular reaction according to i) and/or ii) in the presence of lipase B from *Candida antarctica* and/or, according to iii), in the presence of a lipase from the *porcine pancreas*, a lipase from *Burkholderia* species, a lipase from *Pseudomonas cepacia* or a lipase from *Pseudomonas* species.

More preferably, in this separation process of cis/trans mixtures, the ring A is cis-1,3-cyclohexyl, where the carbon atom of the ring A which has the OH substituent has R configuration, and Z1 and Z2 are each —C(O)—($C_1$-$C_3$-alkyl).

The present invention further provides the compounds of the formula (IIIa) obtainable as intermediates in step d) of the process according to the invention

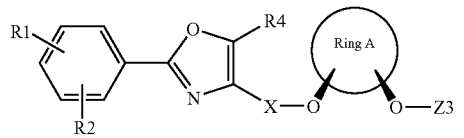
(IIIa)

in which:
R1, R2, R4 are each independently H, F, Cl, Br, OH, $NO_2$, $CF_3$, $OCF_3$, $C_1$-$C_6$-alkyl or —O—($C_1$-$C_6$-alkyl),
X is $C_1$-$C_6$-alkyl in which one or more carbon atoms in the alkyl group may be replaced by oxygen atoms,
Ring A is $C_3$-$C_8$-cycloalkyl or $C_3$-$C_8$-cycloalkenyl, in which one or more carbon atoms in the cycloalkyl or cycloalkenyl rings may be replaced by oxygen atoms,
Z3 is a base-stable and acid-labile protecting group.

Preferred compounds of the formula (IIIa) have the following definitions:
R1, R2, R4 are each independently H, F, Cl, Br, OH, $NO_2$, $CF_3$, $OCF_3$, $C_1$-$C_6$-alkyl or —O—($C_1$-$C_6$-alkyl),
X is $C_1$-$C_3$-alkyl,
Ring A is cyclopentyl, cyclohexyl or cycloheptyl,
Z3 is a base-stable and acid-labile protecting group.

More preferred compounds of the formula (IIIa) have the following definitions:
Ring A is cyclohexyl in which the X-containing and the Z3-containing substituents are in the cis-1,3-arrangement relative to the cyclohexyl fragment,
R1, R2 and R4 are each independently H, F, Cl, $C_1$-$C_3$-alkyl or —O—($C_1$-$C_3$-alkyl),
Z3 is tetrahydropyranyl,
X is methyl.

Particularly preferred compounds of the formula (IIIa) have the following definitions:
Ring A is cyclohexyl in which the X-containing and the Z3-containing substituents are in the cis-1,3-arrangement relative to the cyclohexyl fragment, and the carbon atom of the ring A which is substituted by —O—Z3 has R configuration,
R1, R2 and R4 are each independently H, F, Cl, $C_1$-$C_3$-alkyl or —O—($C_1$-$C_3$-alkyl),
Z3 is tetrahydropyranyl,
X is methyl.

The present invention further provides the compounds of the formula (IIIb) obtainable as intermediates in step d) of the process according to the invention

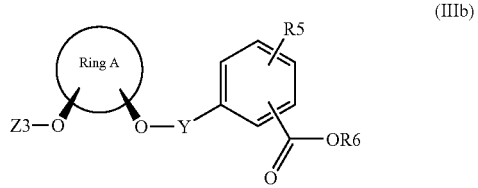
(IIIb)

in which:
R5 is independently H, F, Cl, Br, OH, $NO_2$, $CF_3$, $OCF_3$, $C_1$-$C_6$-alkyl or —O—($C_1$-$C_6$-alkyl),
R6 is $C_1$-$C_6$-alkyl or benzyl, which may optionally be substituted by F, Cl, Br, OH, $NO_2$, $CF_3$, $OCF_3$, $C_1$-$C_6$-alkyl or —O—($C_1$-$C_6$-alkyl),
Y is $C_1$-$C_6$-alkyl in which one or more carbon atoms in the alkyl group may be replaced by oxygen atoms,
Ring A is $C_3$-$C_8$-cycloalkyl or $C_3$-$C_8$-cycloalkenyl, in which one or more carbon atoms in the cycloalkyl or cycloalkenyl rings may be replaced by oxygen atoms,
Z3 is a base-stable and acid-labile protecting group.

Preferred compounds of the formula (IIIb) have the following definitions:
Ring A is cyclohexyl in which the X-containing and the Z3-containing substituents are in the cis-1,3-arrangement relative to the cyclohexyl fragment, and the carbon atom of the ring A which is substituted by —O—Z3 has R configuration,
R5 is H, F, Cl, $C_1$-$C_3$-alkyl or —O—($C_1$-$C_3$-alkyl),
R6 is $C_1$-$C_6$-alkyl or benzyl,
Z3 is tetrahydropyranyl,
Y is methyl.

The present invention further provides the compounds of the formula (VIII) obtainable as intermediates in step b) of the process according to the invention

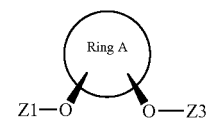
(VIII)

in which:
Ring A is $C_3$-$C_8$-cycloalkyl or $C_3$-$C_8$-cycloalkenyl, in which one or more carbon atoms in the cycloalkyl or cycloalkenyl rings may be replaced by oxygen atoms,
Z1 is an acid-stable protecting group
Z3 is a base-stable and acid-labile protecting group.

Preferred compounds of the formula (VIII) have the following definitions:
Ring A is cyclopentyl, cyclohexyl or cycloheptyl,
Z1 is —C(O)—($C_1$-$C_3$-alkyl),
Z3 is tetrahydropyranyl or methoxyisopropyl.

More preferred compounds of the formula (VIII) have the following definitions:
Ring A is cyclohexyl in which the Z1-containing and the Z3-containing substituents are in the cis-1,3-arrangement relative to the cyclohexyl fragment,
Z1 is —C(O)$CH_3$,
Z3 is tetrahydropyranyl.

Particularly preferred compounds of the formula (VIII) have the following definitions:

Ring A is cyclohexyl in which the Z1-containing and the Z3-containing substituents are in the cis-1,3-arrangement relative to the cyclohexyl fragment, and the carbon atom of the ring A which is substituted by —O—Z3 has R configuration, Z1 is —C(O)CH$_3$, Z3 is tetrahydropyranyl.

As described above, the compounds of the formulae (IIIa) and (IIIb) can be prepared according to steps a) to d) of the process according to the invention. In this regard, the same remarks apply as for the preparation of the compounds of the formula (I). The same also applies for the compounds of the formula (VIII) which can be prepared by steps a) to b) of the process according to the invention. All of these intermediates are consequently also suitable in some cases as starting compounds for the synthesis of PPAR activators of the formula (I).

The examples below serve to illustrate the present invention in more detail. It will be appreciated that every suitable combination of the compounds of the invention with one or more of the aforementioned compounds and optionally one or more other pharmacologically active substances is regarded as falling within the protection conferred by the present invention. The examples are provided to better describe and more specifically set forth the compounds, processes and methods of this invention. It is to be recognized that they are for illustrative purposes only however, and should not be interpreted as limiting the spirit and scope of the invention as later recited by the claims that follow.

EXAMPLES

GC Analysis

Determination of the conversion: Supelco BetaDex325 (30 m×0.25 mm×0.25 μm), carrier gas H$_2$ (1.2 ml/min), inj. 250° C., FID, oven temperature 130° C. isothermal, split 100:1.

Retention times: 10.9 min cis-1-acetoxycyclohexan-3-ol, 14.6 min cis-1,3-diacetoxycyclohexane, 12.6 & 12.8 min trans-1,3-diacetoxycyclohexane.

To determine the enantiomeric excess of cis-1S-acetoxy-cyclohexan-3R-ol, derivatization is effected with heptafluorobutyric anhydride: 2 mg of the sample are dissolved in 0.1 ml of heptafluorobutyric anhydride and the reaction mixture is kept at 70° C. for 10 minutes. The sample is concentrated by evaporation to dryness in a nitrogen stream and taken up again in 0.5 ml of methylene chloride. Retention times: 24.4 min, derivative of cis-1S-acetoxycyclohexan-3R-ol with heptafluorobutyric acid; 25.2 min, derivative of cis-1R-acetoxycyclohexan-3S-ol with heptafluorobutyric acid;

Supelco BetaDex325 (30 m×0.25 mm×0.25 μm), carrier gas: He (1.5 ml/min), inj. 230° C., FID, oven temperature 100° C. isothermal, split 50:1.

Example 1

Reaction of a cis/trans Mixture of cyclohexane-1,3-diol with Vinyl Acetate 4 mg of a 60 to 40 mixture of cis/trans-cyclohexane-1,3-diol are dissolved in 1 ml of vinyl acetate and 5 mg of enzyme according to table 1 are added. The mixture is heated at 25° C. and samples are taken after 21 and 45 h.

TABLE 1

| Trade name | Organism | Manufacturer | NCBI GenBank Accession No./Patent document |
|---|---|---|---|
| Chirazyme L1 lyo. | Burkholderia cepacia | Roche Diagnostics | AAT85572 |
| Chirazyme L1 c.f. | Burkholderia cepacia | Roche Diagnostics | AAT85572 |
| Chirazyme L2 lyo. | Candida antarctica, Fraction B | Roche Diagnostics | CAA83122; EP-A 287 634 |
| Chirazyme L2 c.f. C2 | Candida antarctica, Fraction B | Roche Diagnostics | CAA83122 |
| Chirazyme L2 c.f. C3 | Candida antarctica, Fraction B | Roche Diagnostics | CAA83122 |
| Chirazyme L7 lyo. | Porcine pancreas | Roche Diagnostics | P00591 |
| Lipase PS | Pseudomonas cepacia | Amano Enzymes | EP-A 331,376 |
| Lipase AH | Pseudomonas sp. | Amano Enzymes | |

The enzymes Chirazyme L2 lyo., Chirazyme L2 c.f. C2 and Chirazyme L2 c.f. C3 preferentially form the cis monoacetates. In addition, the enzymes Chirazyme L7 lyo., Chirazyme L1 lyo., Chirazyme L1 c.f., Lipase PS and Lipase AH surprisingly preferentially catalyze the formation of cis diacetate from cis-cyclohexane-1,3-diol with simultaneously high conversion, whereas the trans compound is predominantly converted only to the trans monoacetate (table 2).

The mixtures of monoacetate and diacetate formed in the case of the particular enzymes may then be separated, for example, by extraction or distillation. This also succeeds in removing cis-1,3-diacetoxycyclohexane from commercially available cis/trans mixtures of cyclohexane-1,3-diol.

TABLE 2

| 1) Enzyme | 2) Conversion | 3) Monoacetate | 4) Diacetate | 5) Proportion of cis-diacetate from 4) |
|---|---|---|---|---|
| Chirazyme L7 lyo. | 94% (45 h) | 34% (trans) | 58.8% | 98.2% |
| Chirazyme L1 c.f. | 100% (21 h) | 52.7% (trans) | 47.3% | 94.1% |
| Lipase PS | 100% (45 h) | 59.8% (trans) | 40.2% | 96.1% |
| Lipase AH | 84% (45 h) | 44.3% (trans) | 55.7% | 100% cis |
| Chirazyme L2 c.f. C3 | 100% (21 h) | 92.7% (cis) | 7.3% | 50% |

Example 2

Reaction of a cis/trans Mixture of cyclohexane-1,3-diol with Vinyl Acetate to Give 1,3-diacetoxycyclohexane 30 g of a 60 to 40 mixture of cis/trans-cyclohexane-1,3-diol are dissolved in 900 ml of methyl tert-butyl ether, 100 ml of vinyl acetate are added and 1.7 g of lipase (Chirazyme L1 lyo.) are added (20° C.). After 24 h, the protein is filtered off and the solvent is removed. The remaining oil is taken up in 1000 ml of cyclohexane and washed four times with 150 ml of water. The organic phase is removed on a rotary evaporator.

10 g of cis-1,3-diacetoxycyclohexane are obtained as an oil (23% yield based on the cis/trans mixture, 95% cis).

Example 3

Chemical Acylation of a cis/trans Mixture of cyclohexane-1,3-diol to Give 1,3-diacetoxycyclohexane with Subsequent Enzymatic Desymmetrization to Give cis-1S-acetoxycyclohexan-3R-ol Chemical Acylation cis/trans-Cyclohexane-1,3-diol is converted by simple acylation methods with acetic anhydride or with acetyl chloride, as are known, for example, from Organikum page 405-7, 16th edition, 1986, VEB Deutscher Verlag der Wissenschaften (Berlin), to cis/trans-1,3-diacetoxycyclohexane.

Enzymatic Desymmetrization 21 g of a 96 to 4 mixture of cis/trans-1,3-diacetoxycyclohexane and 0.2 g of Chirazyme L2 lyo. are added at 25° C. to 150 ml of 0.1 M potassium phosphate buffer (pH 7.0). The pH is kept at 7.0 by addition of 10 M KOH and the reaction mixture is stirred for 5 hours. The reaction mixture is then extracted three times with 100 ml each time of methylene chloride and the solvent is removed on a rotary evaporator. 15.8 g of cis-1S-acetoxycyclohexan-3R-ol are obtained (yield 83% based on the cis/trans mixture, ee>99%). The absolute configuration was assigned by means of the chiral HPLC analysis at a later synthetic stage of cis-3S-(2-(4-fluorophenyl)oxazol-4-ylmethoxy)cyclohexan-1R-ol (example 8) by comparison with known reference material.

The scheme III which follows is intended to illustrate the preparation process according to the invention for a specific example (10) of compounds of the formula (I).

Scheme III

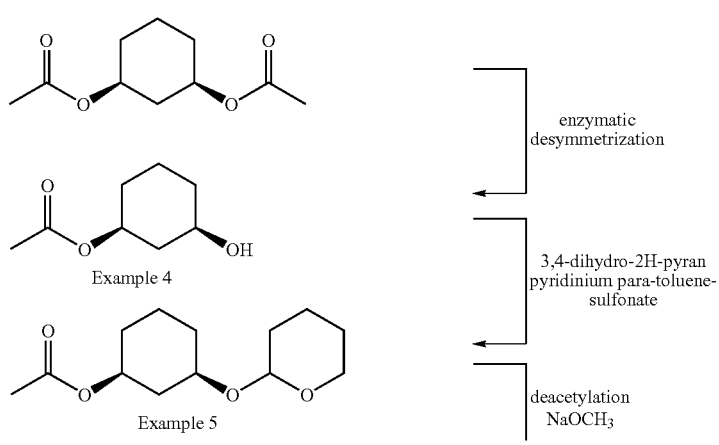

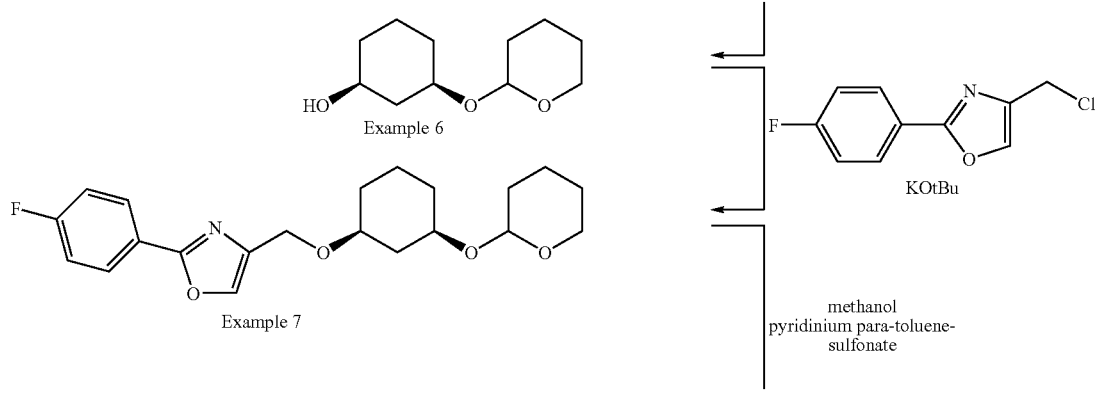

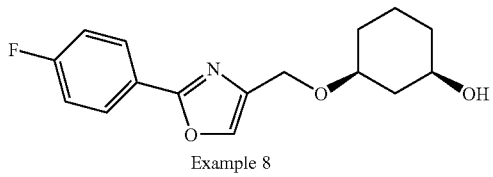

Example 8

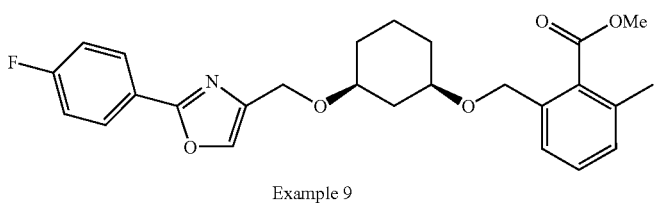

Example 9

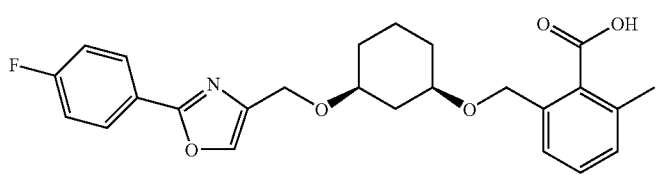

Example 10

Example 4

Chemical Acylation of cis-cyclohexane-1,3-diol to cis-1,3-diacetoxycyclohexane with Subsequent Enzymatic Desymmetrization to Give cis-1S-acetoxycyclohexan-3R-ol Chemical Acylation cis-Cyclohexane-1,3-diol is converted by simple acylation methods with acetic anhydride or with acetyl chloride, as are known, for example, from Organikum page 405-7, 16th edition, 1986, VEB Deutscher Verlag der Wissenschaften (Berlin), to cis-1,3-diacetoxycyclohexane.

Enzymatic Desymmetrization 166 g of cis-1,3-diacetoxycyclohexane and 1.6 g of Chirazyme L2 lyo. are added to 1 l of 0.1 M potassium phosphate buffer (pH 6.8), and the pH is kept constant by addition of 10 M KOH. The reaction mixture is kept at 35° C. for 6 hours and then heated to 75° C. for 1 hour. Subsequently, the mixture is cooled to 8° C. and the reaction mixture is left to stand overnight. The protein is filtered off and the reaction mixture is extracted twice with 500 ml each time of toluene. The solvent is removed on a rotary evaporator. 121.3 g of cis-1S-acetoxycyclohexan-3R-ol are obtained as a colorless oil (87% yield, >99% ee).

Example 5

Introduction of the tetrahydropyranyl (THF) Protecting Group to Give cis-1S-acetoxy-3R—(O-tetrahydropyranyl)cyclohexane 25 g of 87% (138 mmol) cis-1S-acetoxycyclohexan-3R-ol (>99% ee) are heated with 15.6 g (166 mmol) of 3,4-dihydro-2H-pyran in the presence of 1.76 g (0.05 eq.) of pyridinium para-toluenesulfonate in 125 ml of toluene to from 50 to 60° C. with stirring for 1 hour. The quantitative reaction is monitored by means of GC analysis. The reaction mixture is cooled and the precipitated pyridinium para-toluenesulfonate is filtered off. The removal of the pyridinium para-toluenesulfonate by a filtration is not absolutely necessary, since sodium methoxide used in excess in the subsequent deacetylation neutralizes the acidic pyridinium para-toluenesulfonate salt and the deacetylation is thus not affected. The resulting filtrate is used without further purification in the subsequent deacetylation to cis-3R—(O-tetrahydropyranyl)cyclohexan-1S-ol. Concentration of the filtrate results in an oil, the main component present being cis-1S-acetoxy-3R—(O-tetrahydropyranyl)cyclohexane with a molar mass of 242.32 ($C_{13}H_{22}O_4$); MS (EI): 241 (M–H$^+$).

Example 6

Deacetylation to Give cis-3R—(O-tetrahydropyranyl)cyclohexan-1S-ol

The toluenic solution of cis-1S-acetoxy-3R—(O-tetrahydropyranyl)cyclohexane from example 5 is admixed with 115 ml of methanol and reacted with 7.48 g (0.3 eq.) of 30% sodium methoxide-methanol solution. The quantitative deacetylation may be monitored by means of GC analysis. The workup may be effected either by method A) or B):

Method A)

After stirring at room temperature for approx. 2 hours, the reaction mixture is admixed with 600 ml of water. After the aqueous phase has been removed, the toluene phase is extracted 3 times more with 600 ml of water in each case. The aqueous phases are combined, saturated with NaCl and extracted three times with in each case 600 ml of toluene. The other cis-1,3-cyclohexanediol derivatives which occur during the process, i.e. those starting materials, by-products or precursors which do not correspond to example 6 or to the by-product formed with 2 THP protecting groups, remain as water-soluble compounds in the aqueous phase. The organic phases are combined and concentrated under reduced pressure. cis-3-(O-Tetrahydropyranyl)cyclohexan-1S-ol is obtained as a colorless oil with a purity of >97% and a yield of >96% based on cis-1S-acetoxycyclohexan-3R-ol. The thus prepared cis-3R—(O-tetrahydro-pyranyl)cyclohexan-1S-ol has a molecular weight of 200.28 ($C_{11}H_{20}O_3$); MS (EI): 199 (M−H$^+$).

Method B)

After stirring at room temperature for approx. 2 hours, the reaction mixture is admixed with 200 ml of water and the biphasic mixture is stirred for 1 hour. Excess 3,4-dihydro-2H-pyran, methanol, toluene and water are distilled off at an internal temperature up to 65° C. at from 300 to 150 mbar. The viscous residue is taken up with 90 ml of toluene and 14 ml of water, and admixed with 25 g of sodium chloride. After this biphasic mixture has been stirred, the phases are separated and the aqueous phase is extracted with a further 30 ml of toluene. The other cis-1,3-cyclohexanediol derivatives which occur during the process, i.e. those starting materials, by-products or precursors which do not correspond to example 6 or to the by-product formed with 2 THP protecting groups, remain as water-soluble compounds in the aqueous phase. The organic phases are combined and concentrated under reduced pressure. cis-3-(O-Tetrahydropyranyl)cyclohexan-1S-ol is obtained as a colorless oil with a purity of >95% and a yield of >95% based on cis-1S-acetoxycyclohexan-3R-ol. The cis-3R—(O-tetrahydropyranyl)cyclohexan-1S-ol prepared in this way has a molecular weight of 200.28 ($C_{11}H_{20}O_3$); MS (EI): 199 (M−H$^+$).

Example 7

Alkylation with 4-(chloromethyl)-2-(4-fluorophenyl) oxazole to Give cis-1S-(2-(4-fluorophenyl)oxazol-4-ylmethoxy)-3R—O-tetrahydropyranyl-cyclohexane 1.5 g (7.2 mmol) of cis-3R—(O-tetrahydropyranyl)cyclohexan-1S-ol are heated in 40 ml of toluene with 1.17 g (10.1 mmol) of potassium tert-butoxide to 55° C. with stirring for 20 min. A toluenic solution of 1.74 g (7.9 mmol) of 4-(chloromethyl)-2-(4-fluorophenyl)oxazole in 26 ml of toluene is then added dropwise at 55° C. to the reaction solution. On completion of addition, the reaction mixture is stirred at 55° C. for about 5 hours. The reaction is monitored by HPLC. The reaction solution is subsequently admixed with 20 ml of water with vigorous stirring. Concentration of the combined organic phases results in a brown oil having a 74% purity of cis-1-(2-(4-fluorophenyl)oxazol-4-ylmethoxy)-3-O-tetrahydropyranylcyclohexane having a molecular weight of 375.44 ($C_{21}H_{26}FNO_4$); MS (EI): 375.

The combined organic phases may also be used without further purification in the subsequent detachment of the tetrahydropyranyl protecting group to give cis-3S-(2-(4-fluorophenyl)oxazol-4-ylmethoxy)cyclohexan-1R-ol.

Example 8

Removal of the tetrahydropyranyl Protecting Group to Give cis-3S-(2-(4-fluorophenyl)oxazol-4-ylmethoxy)cyclohexan-1R-ol 2.3 g (4.53 mmol) of 74% cis-3S-(2-(4-fluorophenyl)oxazol-4-ylmethoxy)-cyclohexan-1R-ol are stirred in 9 ml of toluene with 3 ml of methanol in the presence of 113 mg (0.1 eq.) of pyridinium para-toluenesulfonate at 55° C. for 6 hours. Subsequently, the reaction solution is extracted with 10 ml of sat. aqueous NaCl solution. In this extraction, any 1,3-cyclohexanediol present, which stems from any by-product which has been formed in example 5 and has 2 THP protecting groups, remains in the aqueous phase. The organic phase is concentrated under reduced pressure. The resulting brown highly viscous oil is stirred with a little diisopropyl ether. After several hours, 44% cis-3-(2-(4-fluorophenyl)oxazol-4-ylmethoxy)cyclohexanol crystallizes with >99% ee and a purity of 99%. After the mother liquor has been concentrated, a further 24% cis-3-(2-(4-fluorophenyl)oxazol-4-ylmethoxy) cyclohexanol crystallizes with >99% ee, but with a purity of 89%. Although further concentration of the mother liquors can afford still further cis-3S-(2-(4-fluorophenyl)oxazol-4-ylmethoxy)cyclohexan-1R-ol in crystalline form, the impurities also increase in the crystallized products with every further concentration of the mother liquors. Simple chromatography with ethyl acetate/toluene of the cis-3S-(2-(4-fluorophenyl)oxazol-4-ylmethoxy)-cyclohexan-1R-ol obtained above as a brown oil leads alternatively to substantially better yields. Chromatography and concentration under reduced pressure result in cis-3S-(2-(4-fluorophenyl)oxazol-4-ylmethoxy)cyclohexan-1R-ol with >99% ee as white crystals. The resulting cis-3S-(2-(4-fluorophenyl)oxazol-4-ylmethoxy)-cyclohexan-1R-ol has a molecular weight of 291.32 ($C_{16}H_{18}FNO_3$); MS (TOF MS ES+): 291.9 (M=H$^+$).

Example 9

Alkylation with methyl 2-(bromomethyl)-6-methylbenzoate to Give methyl cis-2-(3S-(2-(4-fluorophenyl)oxazol-4-ylmethoxy)-cyclohexyl-1R-oxymethyl)-6-methylbenzoate 5 g (17.2 mmol) of cis-3S-(2-(4-fluorophenyl)oxazol-4-ylmethoxy)cyclohexan-1R-ol are dissolved in 175 ml of chlorobenzene and admixed at 0° C. with 3.54 g (30.9 mmol) of potassium tert-butoxide. Alternatively, it also possible to initially charge cis-3S-(2-(4-fluorophenyl)oxazol-4-ylmethoxy)cyclohexan-1R-ol and potassium tert-butoxide as solids, and to admix them at 0° C. with 175 ml of chlorobenzene. Within 20 min, 9.54 g (18.9 mmol) of methyl 2-bromomethyl-6-methylbenzoate are added dropwise as a 50% cyclohexane solution at 0° C. with stirring. After stirring at 0° C. overnight, the reaction solution is extracted three times with 40 ml each time of water. The organic phase is dried over magnesium sulfate and concentrated under reduced pressure. This results in a brown oil comprising from 80 to 90% of methyl cis-2-(3S-(2-(4-fluorophenyl)oxazol-4-ylmethoxy)-cyclohexyl-1R-oxymethyl)-6-methylbenzoate which can be used without further purification in the subsequent hydrolysis. The resulting methyl cis-2-(3S-(2-(4-fluorophenyl)oxazol-4-ylmethoxy)cyclohexyl-1R-oxymethyl)-6-methylbenzoate has a molecular weight of 453.52 ($C_{26}H_{28}FNO_5$); MS (ESI): 454 (M+H$^+$).

Example 10

Hydrolysis and Release by Acidification of the carboxyl Function to Give cis-2-(3S-(2-(4-fluorophenyl)oxazol-4-ylmethoxy)cyclohexyl-1R-oxymethyl)-6-methylbenzoic Acid

Example 10a 7.79 g (15.1 mmol) of 88% methyl cis-2-(3S-(2-(4-fluorophenyl)oxazol-4-ylmethoxy)cyclohexyl-1R-oxymethyl)-6-methylbenzoate are stirred with 2.99 g (45.3 mmol) of 85% potassium hydroxide in 78 ml of tert-butanol at 50° C. overnight. Subsequently, 78 ml of water are added three times and approx. 80 ml of solvent are distilled off in each case under reduced pressure until a cloudy, light yellow product solution results. This solution is extracted three times with in each case 24 ml of methyl tert-butyl ether. After the organic phase has been removed, the aqueous solution is admixed with 50 ml of acetone and acidified with 2 M hydrochloric acid to a pH of 4-5. The solution is stirred at 0-5° C. to form cis-2-(3S-(2-(4-fluorophenyl)oxazol-4-ylmethoxy)cyclohexyl-1R-oxymethyl)-6-methylbenzoic acid as a white crystalline solid (purity>95%) which can be removed by a filtration. The cis-2-(3S-(2-(4-fluorophenyl)oxazole-4-ylmethoxy)cyclohexyl-1R-oxymethyl)-6-methylbenzoic acid obtained as a white crystalline solid with a yield >80%, and an enantiomeric excess of >99% and a purity of >95% may be crystallized from toluene for further purification. Instead of toluene, other solvents, for example n-butyl acetate, alcohols and alcohol/water mixtures, may also be used for the recrystallization.

The resulting cis-2-(3S-(2-(4-fluorophenyl)oxazole-4-ylmethoxy)cyclohexyl-1R-oxy-methyl)-6-methylbenzoic acid has a molecular weight of 439.18 ($C_{25}H_{26}FNO_5$); MS (TOF MS ES+): 440.2 (M+H$^+$).

Example 10b 11.88 g (18.9 mmol) of 72% methyl cis-2-(3S-(2-(4-fluorophenyl)oxazol-4-ylmethoxy)cyclohexyl-1R-oxymethyl)-6-methylbenzoate are stirred with 6.23 g (94.4 mmol) of 85% potassium hydroxide and 6 ml of water in 113 ml of tert-butanol at 70° C. overnight. Subsequently, three times 85 ml of water are added and in each case approx. 85 ml of solvent are distilled off under reduced pressure. The residue is extracted three times with 36 ml each time of methyl isobutyl ketone. The combined water phases are adjusted to pH 8 with 35 ml of 2 M HCl and admixed with 21 ml of n-butyl acetate. A further 10.5 ml of 2 M HCl are used to adjust the 2-phase mixture to pH 4 and it is heated to 90° C. The phases are separated in a preheated separating funnel. The organic phase is heated to 90° C. with activated carbon and filtered. The filtrate is cooled to room temperature, in the course of which cis-2-(3S-(2-(4-fluorophenyl)oxazol-4-ylmethoxy)cyclohexyl-1R-oxymethyl)-6-methylbenzoic acid crystallizes as a white solid (purity>90%). The cis-2-(3S-(2-(4-fluorophenyl)oxazol-4-ylmethoxy)cyclohexyl-1R-oxymethyl)-6-methylbenzoic acid obtained with a yield of 75% and an enantiomeric excess of >99% is crystallized from n-butyl acetate for further purification, which results in a purity of >97% with an enantiomeric excess of >99%. The resulting cis-2-(3S-(2-(4-fluorophenyl)oxazol-4-ylmethoxy)cyclohexyl-1R-oxymethyl)-6-methylbenzoic acid has a molecular weight of 439.18 ($C_{25}H_{26}FNO_5$); MS (TOF MS ES+): 440.2 (M+H$^+$).

The examples 11 to 14 which follow show the synthesis of a further compound of the formula (I).

Example 11

Alkylation with 4-(chloromethyl)-2-(3-methoxyphenyl)-5-methyloxazole to give cis-1S-(2-(3-methoxyphenyl)-5-methyl-oxazol-4-ylmethoxy)-3R—O—tetrahydropyranylcyclohexane A suspension of 13.3 g (115 mmol) of potassium tert-butoxide in 140 ml of toluene is heated to 55° C. with stirring. A solution of 8.58 g (40.2 mmol) of cis-3R—(O-tetrahydropyranyl)cyclohexan-1S-ol (example 6) in 88.5 ml of toluene is added dropwise at 55° C. with stirring for 15 min. On completion of addition, the mixture is stirred at 55° C. for a further 15 min. 52.24 g (40 mmol) of 4-(chloromethyl)-2-(3-methoxyphenyl)-5-methyloxazole in toluene (18.2% solution) are then added dropwise at 55° C. over 45 min. The mixture is stirred at 55° C. for a further one hour. Subsequently, the reaction mixture is admixed with 60 ml of water and 30 ml of saturated sodium chloride solution and cooled to room temperature with stirring. The phases are separated and the organic phase is concentrated on a rotary evaporator. The oily residue is purified by silica gel chromatography with 3:1 toluene/ethyl acetate. Concentration under reduced pressure results in an oil of cis-1-(2-(3-methoxyphenyl)-5-methyloxazol-4-ylmethoxy)-3-O-tetrahydropyranyl-cyclohexane with a molecular weight of 401.5 ($C_{23}H_{31}FNO_5$); MS (EI): 401 (M$^+$).

The toluenic solution of cis-1-(2-(3-methoxyphenyl)-5-methyloxazol-4-ylmethoxy)-3-O-tetrahydropyranylcyclohexane may also be used without further purification in the subsequent detachment of the tetrahydropyranyl protecting group to give cis-3S-(2-(3-methoxyphenyl)-5-methyloxazol-4-ylmethoxy)cyclohexan-1R-ol, since a solvent change is not necessary.

Example 12

Removal of the tetrahydropyranyl Protecting Group to Give cis-3S-(2-(3-methoxyphenyl)-5-methyloxazol-4-ylmethoxy)-cyclohexan-1R-ol 8.04 g (20 mmol) of cis-1-(2-(3-methoxyphenyl)-5-methyloxazol-4-ylmethoxy)-3-O-tetrahydropyranylcyclohexane are admixed with 13 ml of methanol and 0.3 ml of 30% hydrochloric acid, and subsequently heated to 55° C. for approx. 2 hours. The reaction mixture is admixed with 25 ml of water. After the phase separation, the organic phase is concentrated at 40° C. under reduced pressure. This results in 6.03 g (95% yield) of brown oil which are dissolved in 10 ml of toluene and purified by means of column chromatography with 1:2 toluene/ethyl acetate. After the organic solvents have been removed, 3.25 g (69.8%) of cis-3S-(2-(3-methoxyphenyl)-5-methyloxazol-4-ylmethoxy)cyclohexan-1R-ol are obtained as a brown, viscous oil having the molecular weight of 317.39 ($C_{18}H_{23}FNO_4$); MS (EI): 317 (M$^+$).

Example 13

Alkylation with methyl 2-(bromomethyl)-6-methylbenzoate to Give methyl cis-2-(3S-(2-(3-methoxyphenyl)-5-methyloxazol-4-yl methoxy)cyclohexyl-1R-oxymethyl)-6-methylbenzoate 59 g (89.3 mmol) of cis-3S-(2-(3-methoxyphenyl)-5-methyloxazol-4-ylmethoxy)cyclohexan-1R-ol are dissolved in 825 ml of chlorobenzene and admixed at 0° C. with 17.7 g (158 mmol) of potassium tert-butoxide. Within 20 min, 9.54 g (18.9 mmol) of methyl 2-bromomethyl-6-methylbenzoate as a 50% cyclohexane solution are added dropwise at 0° C. with stirring. After stirring at 0° C. overnight, the reaction solution is admixed with 350 ml of sat. NaCl solution and stirred. The organic phase is removed and concentrated under reduced pressure. This results in a brown oil comprising 80% methyl cis-2-(3S-(2-(3-methoxyphenyl)-5-methyloxazol-4-ylmethoxy)cyclohexyl-1R-oxymethyl)-6-methylbenzoate which can be used without further purification in the subsequent hydrolysis or purified by silica gel chromatography with heptane/ethyl acetate before further reaction. The methyl cis-2-(3S-(2-(3-methoxyphenyl)-5-methyloxazol-4-ylmethoxy)cyclohexyl-1R-oxymethyl)-6-methylbenzoate obtained in 64% yield has a molecular weight of 479.58 ($C_{28}H_{33}NO_6$); MS (TOF MS ES+): 480.2 (M+H$^+$).

Example 14

Hydrolysis and Release by Acidification of the Carboxyl Function to Give cis-2-(3S-(2-(3-methoxyphenyl)-5-methyloxazol-4-ylmethoxy)cyclohexyl-1R-oxymethyl)-6-methylbenzoic Acid Example 14a 7 g (14.6 mmol) of 96.5% methyl cis-2-(3S-(2-(3-methoxyphenyl)-5-methyloxazol-4-ylmethoxy)cyclohexyl-1R-oxymethyl)-6-methylbenzoate are heated with 7 ml of 33% sodium hydroxide solution in 70 ml of ethanol to reflux for 25 h. The reaction mixture is concentrated fully under reduced pressure. The oily residue is dissolved with 71 ml of water and subsequently extracted twice with 35 ml each time of methyl tert-butyl ether. The aqueous product phase is admixed with 70 ml of dichloromethane and stirred for 5 min. 11.9 ml of 30% hydrochloric acid are used to adjust the 2-phase mixture to pH 1. The phases are separated and the water phase is extracted once more with dichloromethane. The collected organic phases are dried over magnesium sulfate and concentrated under reduced pressure. The remaining highly viscous oil is dissolved with 50 ml of diisopropyl ether at 35° C.

After seeding of the solution with 10 mg of cis-2-(3S-(2-(3-methoxyphenyl)-5-methyloxazol-4-ylmethoxy)cyclohexyl-1R-oxymethyl)-6-methylbenzoic acid, crystallization sets in after 30 min and can be improved by cooling to 0-5° C. for several hours. The crystals are filtered off with suction and dried at 40° C. under reduced pressure. The cis-2-(3S-(2-(3-methoxyphenyl)-5-methyloxazol-4-ylmethoxy)cyclohexyl-1R-oxymethyl)-6-methylbenzoic acid obtained with a yield of 72.1%, an enantiomeric excess of >99% and a purity of >99% can be recrystallized from n-butyl acetate for further purification.

The cis-2-(3S-(2-(3-methoxyphenyl)-5-methyloxazol-4-ylmethoxy)cyclohexyl-1R-oxymethyl)-6-methylbenzoic acid obtained has a molecular weight of 465.55 ($C_{27}H_{31}NO_6$); MS (ES+): 466.3 (M+H$^+$).

Example 14b

The hydrolysis of 7.9 g (16.5 mmol) of cis-2-(3S-(2-(3-methoxyphenyl)-5-methyloxazol-4-ylmethoxy)cyclohexyl-1R-oxymethyl)-6-methylbenzoic acid is effected directly after the alkylation of cis-3S-(2-(3-methoxyphenyl)-5-methyloxazol-4-ylmethoxy)cycohexan-1R-ol with methyl 2-bromomethyl-6-methylbenzoate in the presence of potassium tert-butoxide as described in example 13, in 750 ml of chlorobenzene without aqueous workup by adding 7.62 g (115 mmol) of 85% KOH to the reaction mixture and heating to 80° C. within 3 hours. After cooling to room temperature, the reaction mixture is extracted with 30 ml of water. The chlorobenzene solution is subsequently extracted once more with 80 ml of water. The combined water phases are admixed with 40 ml of methylene chloride and adjusted to pH 2 with 10 ml of 2M HCl. After vigorous stirring, the phases are separated and the organic phase is concentrated under reduced pressure. The residue is taken up with diisopropyl ether and worked up analogously as above in example 14a.

The examples 15 to 19 which follow and scheme IV show the synthesis of a further compound of the formula (I).

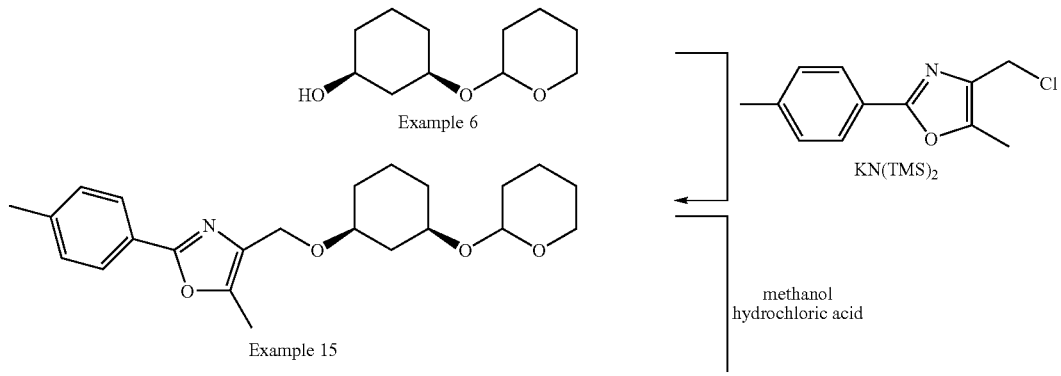

-continued

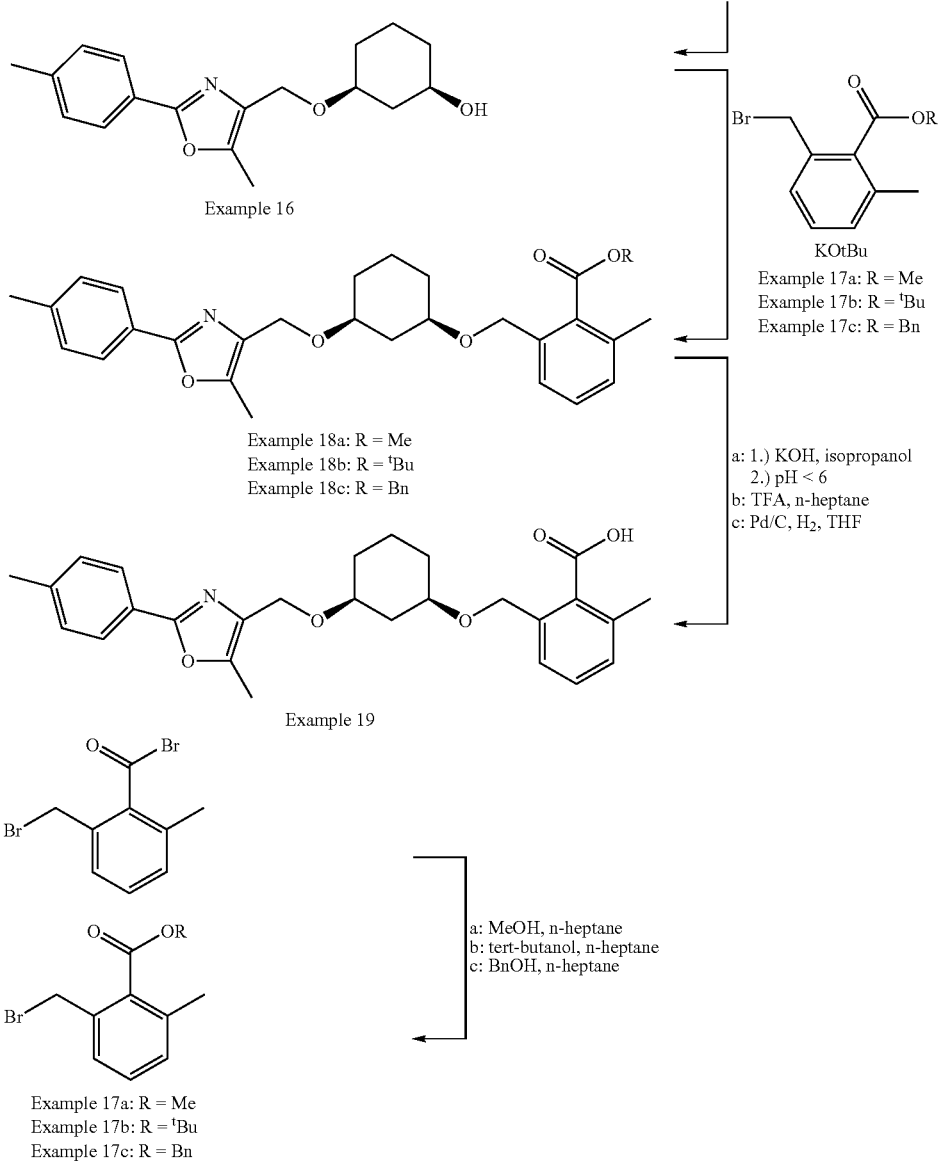

In this further example synthesis, example 6 is reacted with 4-(chloromethyl)-5-methyl-2-p-tolyloxazole in the presence of, for example, alkali metal and alkaline earth metal bases, preferably in the presence of potassium tert-butoxide or potassium bis(trimethylsilyl)amide, to give example 15. Subsequently, example 15 is converted using methanol in the presence of acidic catalysts, for example inorganic acids, toluenesulfonic acid, pyridinium para-toluenesulfonate, Amberlyst H15, preferably with inorganic acids, to example 16. 2-Bromomethyl-6-methylbenzoyl bromide reacts with alcohols such as methanol (Me—OH), tert-butanol (tBu-OH) or benzyl alcohol (Bn-OH) to give example 17a, example 17b and example 17c respectively. Example 16 is alkylated with example 17a, example 17b and example 17c in the presence of, for example, alkali metal and alkaline earth metal bases, preferably in the presence of potassium tert-butoxide, to give example 18a, example 18b and example 18c respectively. Example 18a is hydrolyzed with metal hydroxides, for example alkali metal and alkaline earth metal hydroxides, preferably sodium and potassium hydroxides, in suitable solvents such as water, alcohols or organic solvents, preferably in ethanol or isopropanol. After acidification, for example, with organic or inorganic acids, preferably with inorganic acids, the desired chiral PPAR activator example 19 is isolated. Example 19 is likewise obtained from example 18b by ester cleavage with acidic catalysts, for example inorganic acids or trifluoroacetic acid (TFA), preferably hydrochloric acid or trifluoroacetic acid. Example 18c is converted by hydrogenolysis with a heterogeneous catalyst, preferably a noble metal catalyst and very preferably a palladium catalyst, to example 19. Example 19 is isolated in an optical purity of >99% ee, neither chiral nor achiral chromatography being required for purification. The purification is carried out by crystallization of example 16 and of the PPAR activator example 19, for example from an organic solvent, preferably from diisopropyl ether.

Example 15

Alkylation of cis-3R—(O-tetrahydropyranyl)cyclohexan-1S-ol with 4-(chloromethyl)-5-methyl-2-p-tolyloxazole to Give cis-1S-(2-p-tolyl-5-methyloxazol-4-ylmethoxy)-3R—O-tetrahydropyranylcyclohexane A solution of 110 g (550 mmol) of cis-3R—(O-tetrahydropyranyl)cyclohexan-1S-ol (example 6) in 500 ml of tert-butyl methyl ether and 97 ml of toluene is added with stirring to a suspension of 130 g (652 mmol) of potassium bis(trimethylsilyl)amide in 1.5 l of tert-butyl methyl ether. The reaction mixture is stirred at room temperature for 10 minutes before a solution of 111 g (501 mmol) of 4-(chloromethyl)-5-methyl-2-p-tolyloxazole in 1.5 l of tert-butyl methyl ether is added. The reaction is stirred at 35° C. up to complete conversion (HPLC). An aliquot of the reaction mixture is washed with water, dried over magnesium sulfate and subsequently concentrated fully under reduced pressure. The cis-1S-2-p-tolyl-5-methyloxazol-4-ylmethoxy)-3R—O-tetrahydropyranylcyclohexane prepared in this way has a molecular weight of 385.51 ($C_{23}H_{31}NO_4$); MS (ESI): 302 [M−THP+H$^+$].

Example 16

Detachment of the THP Protecting Group From cis-3S-(2-p-tolyl-5-methyloxazol-4ylmethoxy)-3R—O-tetrahydropyranylcyclohexane to Give cis-3S-(2-p-tolyl-5-methyloxazol-4-ylmethoxy)cyclohexan-1R-ol 100 ml of methanol and then 101 ml of conc. hydrochloric acid are added to the solution of cis-3S-(2-p-tolyl-5-methyloxazol-4ylmethoxy)-3R—O-tetrahydropyranyl-cyclohexane in tert-butyl methyl ether and toluene from example 15. The reaction is stirred at 25° C. On completion of conversion, 1.0 l of water and 101 g (1.2 mol) of sodium hydrogencarbonate are added and the mixture is stirred intensively. After filtration, the aqueous phase is removed and the organic phase is washed three times with 800 ml each time of water. The solvent is distilled off under reduced pressure and the resulting oily residue is taken up in 450 ml of diisopropyl ether. The mixture is stirred at room temperature. The precipitated product is filtered off and washed with a little diisopropyl ether. 56% of cis-3S-(2-p-tolyl-5-methyloxazol-4-ylmethoxy)cyclohexan-1R-ol having a molecular weight of 301.39 ($C_{18}H_{23}NO_3$) is obtained; MS (ESI): 302 [M+H$^+$].

Example 17a

Synthesis of methyl 2-bromomethyl-6-methylbenzoate From 2-bromomethyl-6-methylbenzoyl bromide 200 g (240 mmol) of 2-bromomethyl-6-methylbenzoyl bromide solution (35% solution in heptane) are added to 400 ml of methanol. After stirring at RT for one hour, 400 ml of n-heptane are added. The solution is washed successively with 600 ml of sat. sodium hydrogencarbonate solution and three times with 200 ml each time of water. Subsequently, the solvent is removed fully under reduced pressure. 98.8% of methyl 2-bromomethyl-6-methylbenzoate is obtained as a colorless oil having a purity of 80% (included in the yield) and having a molecular weight of 241.99 ($C_{10}H_{11}BrO_2$); MS (ESI): 243.1 [M+H$^+$].

Example 17b

Synthesis of tert-butyl 2-bromomethyl-6-methylbenzoate 20 g (24 mmol) of 2-bromomethyl-6-methylbenzoyl bromide solution (35% solution in heptane) are added to a mixture of 15 ml of n-heptane and 25 ml of tert-butanol. After stirring at 40° C. for one hour, 400 ml of n-heptane are added. The solution is washed successively with 60 ml of sat. sodium hydrogencarbonate solution and washed four times with 20 ml each time of water. Subsequently, the solvent is removed fully under reduced pressure. When the conversion is quantitative, tert-butyl 2-bromomethyl-6-methylbenzoate is obtained as a virtually colorless oil having 93% purity and having a molecular weight of 284.04 ($C_{13}H_{17}BrO_2$); MS (ESI): 302.1 [M+NH$_4$]$^+$.

Example 17c

Synthesis of benzyl 2-bromomethyl-6-methylbenzoate 24.2 g (221 mmol) of benzyl alcohol are added with ice cooling to 136 g (233 mmol) of 2-bromomethyl-6-methylbenzoyl bromide solution (35% solution in heptane). Subsequently, the mixture is left to stir at RT for one hour. After addition of 500 ml of tert-butyl methyl ether, the organic solution is washed successively with 410 ml of sat. sodium hydrogencarbonate solution and four times with 300 ml each time of water. Subsequently, the solvent is removed fully under reduced pressure. 74 g of benzyl 2-bromomethyl-6-methylbenzoate are obtained as a colorless oil having a purity of 80%. The benzyl 2-bromomethyl-6-methylbenzoate prepared in this way has a molecular weight of 318.02 ($C_{16}H_{15}BrO_2$); MS (ESI): 341.0 [M+Na]$^+$.

Example 18a

Alkylation of cis-3S-(2-p-tolyl-5-methyloxazol-4-ylmethoxy)-cyclohexan-1R-ol with methyl 2-bromomethyl-6-methyl-benzoate to Give methyl 2-methyl-6-[(1R,3S)-3-(5-methyl-2-p-tolyloxazol-4-yl methoxy)cyclohexyloxymethyl]benzoate 50 g (166 mmol) of cis-3S-(2-p-tolyl-5-methyloxazol-4-ylmethoxy)cyclohexan-1R-ol and 30 g (262 mmol) of potassium tert-butoxide are dissolved in 500 ml of THF and the mixture is stirred at RT for 30 minutes. After addition of 500 ml of tert-butyl methyl ether, a solution of 51 g (210 mmol) of methyl 2-bromomethyl-6-methylbenzoate in 310 ml of tert-butyl methyl ether is added. The reaction is stirred at temperatures between 25-30° C. for 1 hour and is quenched by adding 500 ml of hydrochloric acid (0.5 molar). After removal of the aqueous phase, the organic phase is washed three times with 300 ml each time of water. Subsequently, the solvent is removed fully under reduced pressure. 74 g of methyl 2-methyl-6-[(1R,3S)-3-(5-methyl-2-p-tolyloxazol-4-ylmethoxy)cyclohexyloxymethyl]benzoate are obtained as a slightly yellow oil having a purity of 79% and having a molecular weight of 463.57 ($C_{28}H_{33}NO_5$); MS (ESI): 464.37 [M+H]$^+$.

Example 18b

Alkylation of cis-3S-(2-p-tolyl-5-methyloxazol-4-ylmethoxy)-cyclohexan-1R-ol with tert-butyl 2-bromomethyl-6-methyl-benzoate to Give tert-butyl 2-methyl-6-[(1R,3S)-3-(5-methyl-2-p-tolyloxazol-4-ylmethoxy)cyclohexyloxymethyl]benzoate 100 g (332 mmol) of cis-3S-(2-p-tolyl-5-methyloxazol-4-ylmethoxy)cyclohexan-1R-ol and 60 g (524 mmol) of potassium tert-butoxide are dissolved in 1.0 l of THF and the mixture is stirred at RT for 30 minutes. After addition of 1 l of tert-butyl methyl ether, a solution of 120 g (524 mmol) of methyl 2-bromomethyl-6-methylbenzoate in 850 ml of tert-butyl methyl ether is added. The reaction is stirred at temperatures of 40° C. for 30 minutes. Subsequently, the organic phase is washed successively with 1.0 l of water, 250 ml of hydrochloric acid (0.5 molar) and four times with 500 ml each time of aqueous sodium chloride solution (1%). After full removal of the solvent under reduced pressure, 195 g of tert-butyl 2-methyl-6-[(1R,3S)-3-(5-methyl-2-p-tolyloxazol-4-ylmethoxy)cyclohexyloxymethyl]benzoate are obtained as a yellow oil having a purity of 86%. The tert-butyl 2-methyl-6-[(1R,3S)-3-(5-methyl-2-p-tolyloxazol-4-ylmethoxy)cyclohexyloxymethyl]benzoate prepared in this way has a molecular weight of 505.65 ($C_{31}H_{39}NO_5$); MS (ESI): 506.39 [M+H]$^+$.

Example 18c

Alkylation of cis-3S-(2-p-tolyl-5-methyloxazol-4-ylmethoxy)-cyclohexan-1R-ol with benzyl 2-bromomethyl-6-methyl-benzoate to Give benzyl 2-methyl-6-[(1R,3S)-3-(5-methyl-2-p-tolyloxazol-4-ylmethoxy)cyclohexyloxymethyl]benzoate 18 g (157 mmol) of potassium tert-butoxide are added to a solution of 30 g (100 mmol) of cis-3S-(2-p-tolyl-5-methyloxazol-4-ylmethoxy)cyclohexan-1R-ol in 300 ml of THF and the mixture is stirred at RT for 30 minutes. After addition of 44.5 g (112 mmol) of benzyl 2-bromomethyl-6-methylbenzoate (80%), the reaction is stirred at 30° C. for 30 minutes. Subsequently, the reaction is poured onto a solution of 15 ml of hydrochloric acid (32%) in 300 ml of water. After phase separation, the organic phase is concentrated fully under reduced pressure and the residue is taken up in 500 ml of tert-butyl methyl ether. The solution is washed four times with 300 ml each time of water. The solution is removed under reduced pressure and the residue is purified by chromatography on silica gel. Benzyl 2-methyl-6-[(1R,3S)-3-(5-methyl-2-p-tolyloxazol-4-ylmethoxy)cyclohexyloxymethyl]benzoate is obtained in 90% yield as a yellow oil having a molecular weight of 539.68 ($C_{34}H_{37}NO_5$); MS (ESI): 540.41 [M+H]$^+$.

Example 19

Synthesis of 2-methyl-6-[(1R,3S)-3-(5-methyl-2-p-tolyloxazol-4-ylmethoxy)cyclohexyloxymethyl]benzoic Acid by Ester Cleavage a: from methyl methyl-6-[(1R,3S)-3-(5-methyl-2-p-tolyloxazol-4-ylmethoxy)-cyclohexyloxymethyl]benzoate: 97.1 g (165 mmol) of methyl methyl-6-[(1R,3S)-3-(5-methyl-2-p-tolyloxazol-4-ylmethoxy)cyclohexyloxymethyl]benzoate are dissolved in a mixture of 640 ml of isopropanol and 80 ml of water. 47.7 g (809 mmol) of potassium hydroxide are added in portions. The reaction is stirred at 95° C. for 24 hours. Subsequently, the solvent is removed fully under reduced pressure and the residue is taken up in 800 ml of tert-butyl methyl ether and 800 ml of water. Addition of hydrochloric acid (2 M) acidifies the mixture. After phase separation, the organic phase is washed four times with 200 ml each time of water. The organic phase is concentrated under reduced pressure and the residue is stirred with a little diisopropyl ether. The solid is filtered and dried under reduced pressure. 2-methyl-6-[(1R,3S)-3-(5-methyl-2-p-tolyloxazol-4-ylmethoxy)-cyclohexyloxymethyl]benzoic acid is obtained in 57% yield as a crystalline solid.

b: from tert-butyl methyl-6-[(1R,3S)-3-(5-methyl-2-p-tolyloxazol-4-ylmethoxy)-cyclohexyloxymethyl]benzoate: 200 g (396 mmol) of tert-butyl methyl-6-[(1R,3S)-3-(5-methyl-2-p-tolyloxazol-4-ylmethoxy)cyclohexyloxymethyl] benzoate are dissolved in n-heptane. 300 g (2.6 mol) of trifluoroacetic acid are added. The reaction is stirred at RT for 24 hours and subsequently concentrated fully by evaporation. The residue is taken up in 1.0 l of diisopropyl ether and washed four time with 500 ml each time of water. Subsequently, 1.0 l of water is added and a basic pH is established by addition of sodium hydroxide solution (4 M). After phase separation, the aqueous phase is washed twice with 400 ml each time of diisopropyl ether. After addition of 1.6 l of diisopropyl ether, the mixture is acidified with hydrochloric acid (2 M). After phase separation, the organic phase is washed four times with 500 ml each time of water and subsequently concentrated to about a third of the volume. 2-methyl-6-[(1R,3S)-3-(5-methyl-2-p-tolyloxazol-4-ylmethoxy) cyclohexyloxymethyl]benzoic acid precipitates out as a crystalline solid and is filtered off. After drying under reduced pressure, 2-methyl-6-[(1R,3S)-3-(5-methyl-2-p-tolyloxazol-4-ylmethoxy)cyclohexyloxymethyl]benzoic acid is obtained in 66% yield.

c: from benzyl methyl-6-[(1R,3S)-3-(5-methyl-2-p-tolyloxazol-4-ylmethoxy)-cyclohexyloxymethyl]benzoate: 15 g (27.8 mmol) of benzyl methyl-6-[(1R,3S)-3-(5-methyl-2-p-tolyloxazol-4-ylmethoxy)cyclohexyloxymethyl]benzoate are dissolved in 300 ml of THF. 700 mg of palladium on carbon (5%) are added. Subsequently, hydrogenation is effected at standard pressure and RT until no more hydrogen is taken up. The reaction mixture is filtered and the organic phase is subsequently concentrated fully under reduced pressure. The residue is taken up in 150 ml of tert-butyl methyl ether, 150 ml of water and 150 ml of saturated sodium hydrogencarbonate solution. After phase separation, the aqueous phase is washed with 150 ml of tert-butyl methyl ether. Subsequently, 150 ml of diisopropyl ether are added and the mixture is acidified with concentrated hydrochloric acid. After phase separation, the organic phase is washed four times with 100 ml each time of water and then concentrated fully under reduced pressure. The residue is stirred with a little diisopropyl ether. The solid is filtered and dried under reduced pressure. 2-methyl-6-[(1R,3S)-3-(5-methyl-2-p-tolyloxazol-4-ylmethoxy)cyclohexyl-oxymethyl]benzoic acid is obtained in 42% yield as a crystalline solid.

The 2-methyl-6-[(1R,3S)-3-(5-methyl-2-p-tolyloxazol-4-ylmethoxy)cyclohexyloxy-methyl]benzoic acid prepared by the different variants has a molecular weight of 449.55 ($C_{27}H_{31}NO_5$); MS (ESI): 450.29 [M+H]$^+$.

The examples 20 and 21 which follow and also scheme V show the synthesis of a further compound of the formula (I)

Scheme V

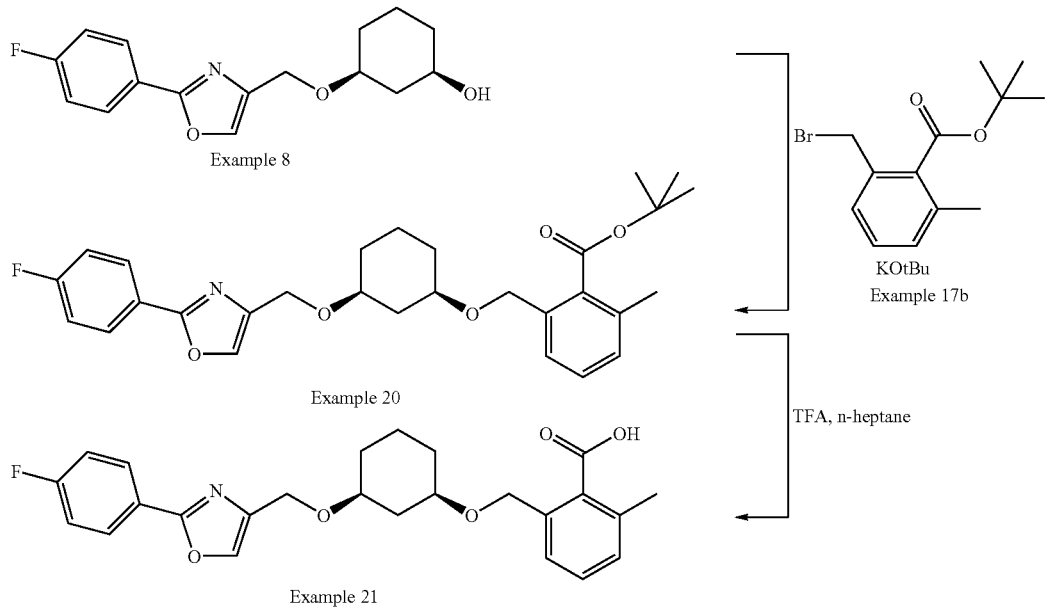

Example 20

Alkylation of cis-3S-(2-(4-fluorophenyl)oxazol-4-yl-methoxy)cyclohexan-1R-ol with tert-butyl 2-bromomethyl-6-methylbenzoate to Give tert-butyl cis-2-(3S-(2-(4-fluorophenyl)oxazol-4-ylmethoxy) cyclohexyl-1R-oxymethyl)-6-methylbenzoate 3.31 g (28 mmol) of potassium tert-butoxide are added to a solution of 5.1 g (17.5 mmol) of cis-3S-(2-(4-fluorophenyl) oxazol-4-ylmethoxy)cyclohexan-1R-ol (example 8) in 50 ml of THF. The mixture is stirred at RT for 30 minutes. 6.83 g (22.8 mmol) of tert-butyl 2-bromomethyl-6-methylbenzoate (95%) (example 17b) are added. The reaction is stirred at RT for 1 hour. 100 ml of water and 17.5 ml of hydrochloric acid (2 M) are added. After phase separation, the organic phase is washed four times with 100 ml each time of water and concentrated fully under reduced pressure. 10.6 g of tert-butyl cis-2-(3S-(2-(4-fluorophenyl)oxazol-4-yl-methoxy)cyclohexyl-1R-oxymethyl)-6-methylbenzoate are obtained as a slightly yellow oil having a purity of 82%. The thus obtained tert-butyl cis-2-(3S-(2-(4-fluorophenyl)oxazol-4-yl-methoxy)cyclohexyl-1R-oxymethyl)-6-methylbenzoate has a molecular weight of 495.59 ($C_{29}H_{34}FNO_5$); MS (ESI): 440.19 [M−tert-butyl+H+H]⁺.

Example 21

Cleavage of the tert-butyl ester of cis-2-(3S-(2-(4-fluorophenyl)oxazol-4-ylmethoxy)cyclohexyl-1R-oxymethyl)-6-methylbenzoate to Give cis-2-(3S-(2-(4-fluorophenyl)oxazol-4-yl-methoxy)cyclohexyl-1R-oxymethyl)-6-methylbenzoic Acid 10.6 g (17.5 mmol) of tert-butyl ester of cis-2-(3S-(2-(4-fluorophenyl)oxazol-4-yl-methoxy)cyclohexyl-1R-oxymethyl)-6-methylbenzoate (82%) are dissolved in 20 ml of dichloromethane. After addition of 10 ml (128 mmol) of trifluoroacetic acid, the reaction is stirred at RT for 16 hours. Subsequently, the reaction is concentrated fully. The residue is taken up in 100 ml of diisopropyl ether and washed six times with 50 ml each time of water. Subsequently, 100 ml of water are added and a basic pH is established by adding sodium hydroxide solution (2 M). After phase separation, the aqueous phase is washed three times with 50 ml each time of diisopropyl ether. 150 ml of diisopropyl ether are then added and the mixture is acidified with hydrochloric acid (2 M). After phase separation, the organic phase is washed three times with 50 ml each time of water and then concentrated fully. The residue is recrystallized from diisopropyl ether. 2.9 g of cis-2-(3S-(2-(4-fluorophenyl)oxazol-4-yl-methoxy)cyclohexyl-1R-oxymethyl)-6-methyl-benzoic acid are isolated as crystals. The thus prepared cis-2-(3S-(2-(4-fluorophenyl)oxazol-4-yl-methoxy)cyclohexyl-1R-oxymethyl)-6-methylbenzoic acid has a molecular weight of 439.48 ($C_{25}H_{26}FNO_5$): MS (ESI): 438.31 [M−H]⁻.

What is claimed is:

1. A process for preparing a compound of the formula (I), comprising the steps according to the following scheme:

Scheme I

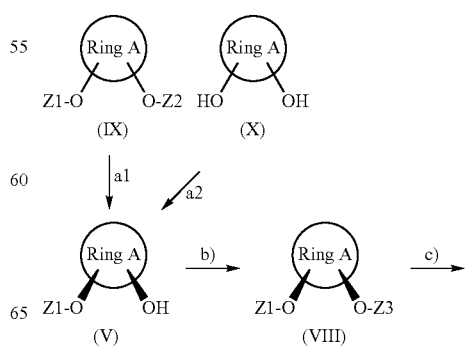

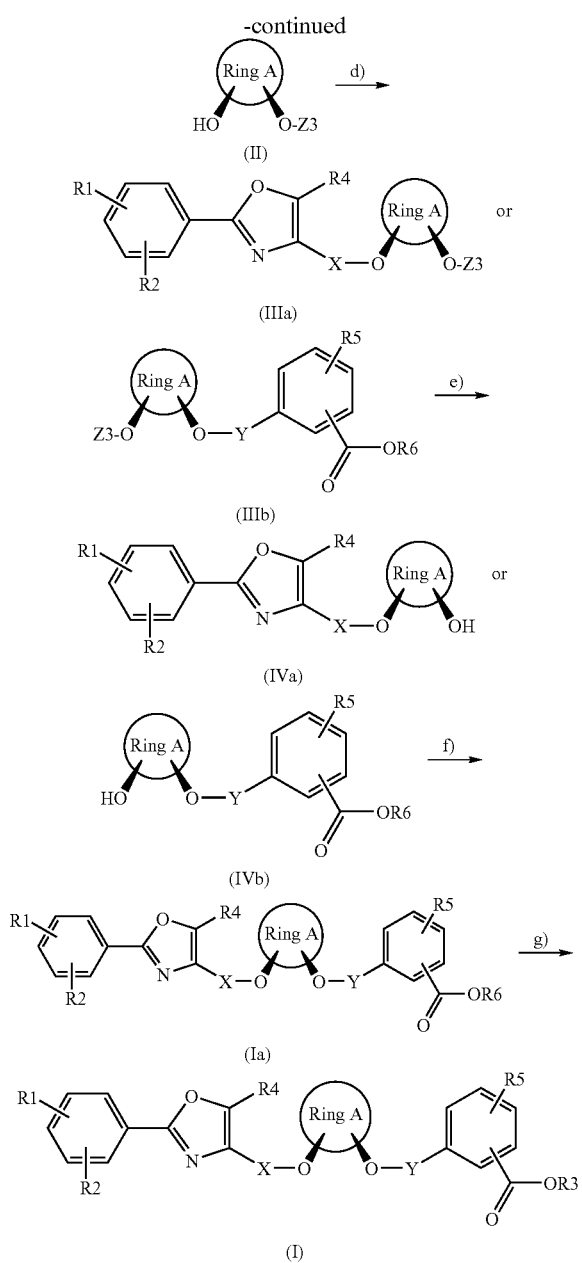

in which, in the individual steps, a1) a compound of the formula (IX) is reacted with water to give a compound of the formula (V) in the presence of lipase enzyme which affords a suitable enantiomeric excess of the compound (V), or a2) a compound of the formula (X) is reacted with at least one acyl donor to give the compound (V) in the presence of lipase enzyme which affords a suitable enantiomeric excess of the compound (V), b) the compound (V) is reacted in the presence of an acidic catalyst with a compound which can form the base-stable and acid-labile protecting group Z3 to give the compound of the formula (VIII) and c) the compound (VIII) is converted in the presence of a nucleophile to a compound of the formula (II), d) the compound (II) is reacted in the presence of a base B1 with a compound of the formula (VI) to give a compound of the formula (IIIa) or with a compound of the formula (VII) to give a compound of the formula (IIIb),

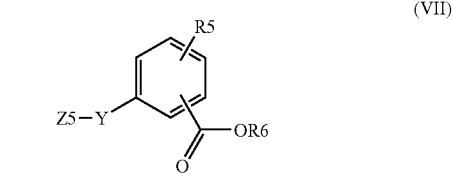

e) the compound (IIIa) is converted to a compound of the formula (IVa) or the compound (IIIb) to a compound of the formula (IVb), the particular reaction being effected with an alcohol in the presence of an acidic catalyst, f) the compound (IVa) is reacted with the compound (VII) or the compound (IVb) with the compound (VI) to give a compound of the formula (Ia) in the presence of the base B1 and g) if appropriate, the compound (Ia) is hydrolyzed or hydrogenolyzed to give the compound (I) when R3 is H, the compounds (IX) and (X) each being present as the pure cis isomer or as cis/trans mixtures, and in which the variables and substituents are each defined as follows:

Ring A is $C_3$-$C_8$-cycloalkyl or $C_3$-$C_8$-cycloalkenyl, in which one or more carbon atoms in the cycloalkyl or cycloalkenyl rings may be replaced by oxygen atoms, R1, R2, R4 and R5 are each independently H, F, Cl, Br, OH, $NO_2$, $CF_3$, $OCF_3$, $C_1$-$C_6$-alkyl or —O—($C_1$-$C_6$-alkyl), R3 is H, $C_1$-$C_6$-alkyl or benzyl, which may optionally be substituted by F, Cl, Br, OH, $NO_2$, $CF_3$, $OCF_3$, $C_1$-$C_6$-alkyl or —O—($C_1$-$C_6$-alkyl), R6 is $C_1$-$C_6$-alkyl or benzyl, which may optionally be substituted by F, Cl, Br, OH, $NO_2$, $CF_3$, $OCF_3$, $C_1$-$C_6$-alkyl or —O—($C_1$-$C_6$-alkyl), X is $C_1$-$C_6$-alkyl, in which one or more carbon atoms in the alkyl group may be replaced by oxygen atoms, Y is $C_1$-$C_6$-alkyl, in which one or more carbon atoms in the alkyl group may be replaced by oxygen atoms, Z1 and Z2 are each independently an acid-stable protecting group, Z3 is a base-stable and acid-labile protecting group, Z4 and Z5 are each independently a leaving group, and B1 is a tertiary alkaline earth metal alkoxide, tertiary alkali metal alkoxide, alkaline earth metal amide, alkali metal amide, alkaline earth metal silazide, alkali metal silazide or alkali metal hydride.

2. The process according to claim 1, wherein the compound (IX) is prepared by i) reacting the compound (X) with at least one acyl donor in the presence of lipase enzyme which affords mainly the cis isomer of the compound (IX), and the trans isomers of the compounds of the formula (V) which may be formed as by-products are removed, or ii) reacting the compound (X) with at least one acyl donor.

3. The process according to claim 1, wherein Z1 and Z2 are each —C(O)—$CH_3$ and Z3 is tetrahydropyranyl or methoxyisopropyl.

4. The process according to claim 1, in which:

Ring A is cyclopentyl, cyclohexyl or cycloheptyl,

R1, R2, R4 and R5 are each independently H, F, Cl, Br, OH, $NO_2$, $CF_3$, —$OCF_3$, $C_1$-$C_6$-alkyl or O—$C_1$-$C_6$-alkyl, R3 is H or $C_1$-$C_6$-alkyl or benzyl, and X and Y are each independently $C_1$-$C_6$-alkyl.

5. The process according to claim 4, in which:

Ring A is cyclohexyl in which the X-containing and the Y-containing substituents of formula (I) are in the cis-1,3-arrangement relative to the cyclohexyl fragment, and X and Y are each methyl.

6. The process according to claim 1, in which a) the compound of the formula (IX) is reacted in the presence of lipase B from *Candida antarctica* with water to give the compound of the formula (V), b) the compound of formula (V) is reacted in the presence of an acidic catalyst with a compound which can form the base-stable and acid-labile protecting group Z3 to give the compound of the formula (VIII), c) the compound of formula (VIII) is converted in the presence of a nucleophile to a compound of the formula (II), d) the compound of formula (II) is reacted in the presence of a base B1 with a compound of the formula (VI) to give a compound of the formula (IIIa), e) the compound of formula (IIIa) is converted to a compound of the formula (IVa), the reaction being effected with an alcohol in the presence of an acidic catalyst, f) the compound of formula (IVa) is reacted with the compound of formula (VII) to give a compound of the formula (Ia) in the presence of the base B1 and g) if appropriate, the compound of formula (Ia) is hydrolyzed or hydrogenolyzed to give the compound of formula (I) when R3 is H, and Ring A is cyclohexyl in which the X-containing and the Y-containing substituents of formula (I) are in the cis-1,3-arrangement relative to the cyclohexyl fragment, and the carbon atom of the ring A which is substituted by the Y-containing substituent has R configuration.

7. The process according to claim 1, wherein the compound of formula (I) is present in an enantiomeric purity of greater than 99%.

* * * * *

UNITED STATES PATENT AND TRADEMARK OFFICE
CERTIFICATE OF CORRECTION

| | | |
|---|---|---|
| PATENT NO. | : 7,803,950 B2 | Page 1 of 1 |
| APPLICATION NO. | : 11/676721 | |
| DATED | : February 20, 2007 | |
| INVENTOR(S) | : Salagnad et al. | |

It is certified that error appears in the above-identified patent and that said Letters Patent is hereby corrected as shown below:

Column 33, claim 1, line 1 reads

"e) pound of the formula (Ma) or with a compound of the", and should read

"e) pound of the formula (IIIa) or with a compound of the"

Column 46, claim 6, line 4 reads

"e) the compound of formula (Ma) is converted to a com-", and should read

"e) the compound of formula (IIIa) is converted to a com-"

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,803,950 B2 | |
| APPLICATION NO. | : 11/676721 | |
| DATED | : February 20, 2007 | |
| INVENTOR(S) | : Salagnad et al. | |

It is certified that error appears in the above-identified patent and that said Letters Patent is hereby corrected as shown below:

Column 44, claim 1, line 1 reads

"e) pound of the formula (Ma) or with a compound of the", and should read

"e) pound of the formula (IIIa) or with a compound of the"

Column 46, claim 6, line 4 reads

"e) the compound of formula (Ma) is converted to a com-", and should read

"e) the compound of formula (IIIa) is converted to a com-"

This certificate supersedes the Certificate of Correction issued November 30, 2010.

Signed and Sealed this
Twenty-fifth Day of January, 2011

David J. Kappos
*Director of the United States Patent and Trademark Office*